United States Patent [19]

Franceschini et al.

[11] Patent Number: 5,006,570

[45] Date of Patent: Apr. 9, 1991

[54] DIHYDROBENZOFURAN- AND CHROMAN-CARBOXAMIDE DERIVATIVES, PROCESSES FOR THE PREPARATION THEREOF AND USE THEREOF AS NEUROLEPTICS

[75] Inventors: Jacqueline Franceschini, L'Hay-Les-Roses; Josette Margarit, Paris, both of France

[73] Assignee: Laboratoires Delagrange, Paris, France

[21] Appl. No.: 8,916

[22] Filed: Jan. 30, 1987

[30] Foreign Application Priority Data

Jan. 30, 1986 [FR] France .................. 86 01279

[51] Int. Cl.$^5$ .............. A61K 31/40; C07D 405/00
[52] U.S. Cl. .................... 514/422; 548/525
[58] Field of Search ............. 548/525; 514/422, 456, 514/469; 549/404, 405, 462, 467

[56] References Cited

U.S. PATENT DOCUMENTS 4,617,314 10/1986 Tahara et al. .............. 514/422
4,829,067 5/1989 Iijima et al. ................ 548/525

FOREIGN PATENT DOCUMENTS 0124783 11/1984 European Pat. Off. .
0147044 7/1985 European Pat. Off. .

OTHER PUBLICATIONS

Florvall et al., "Annulated Benzamide Deriv.", Chemical Abs., vol. 107(7), No. 58841u (1987).
Sun et al., "Method for Controlling Emesis", Chemical Abs. 1, vol. 110 (11), No. 88631e (1989).

Primary Examiner—Mukund J. Shah
Assistant Examiner—E. C. Ward
Attorney, Agent, or Firm—Fitzpatrick, Cella, Harper & Scinto

[57] ABSTRACT

The invention relates to new dihydrobenzofuran- and chroman-carboxamide derivatives of the general formula:

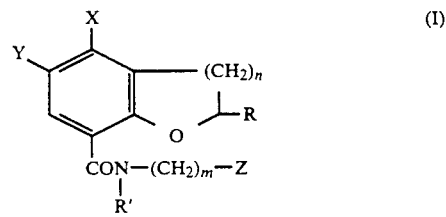

in which R and R' are each hydrogen or methyl; n is 1 or 2; m is 1 or 2;
Z is either

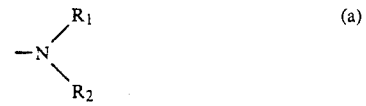

wherein $R_1$ and $R_2$ are lower alkyl,
or

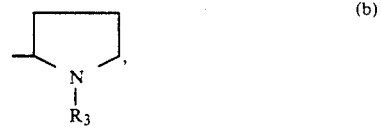

wherein $R_3$ is alkyl, alkenyl, cycloalkyl-alkyl, cycloalkenyl-alkyl, X is H, $NH_2$, methoxy, or methyl and Y is H, Cl, cycloalkylmethylsulfonyl, alkylsulfamoyl or alkylsulfonyl
and to their pharmacologically acceptable acid addition salts and their optical isomers, to the processes for the preparation thereof and to the use thereof as medicaments, especially as neuroleptics.

12 Claims, No Drawings

DIHYDROBENZOFURAN- AND CHROMAN-CARBOXAMIDE DERIVATIVES, PROCESSES FOR THE PREPARATION THEREOF AND USE THEREOF AS NEUROLEPTICS

SUMMARY OF THE INVENTION

The invention relates to new dihydrobenzofuran- and chroman-carboxamide derivatives of formula (I):

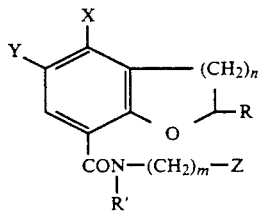

in which:
R and R' are the same or different and are each hydrogen or methyl,
n is equal to 1 to 2,
m is equal to 1 to 2, and
Z is a group of formula (a):

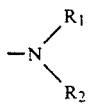

in which $R_1$ and $R_2$ are each lower alkyl, preferably $C_1$-$C_6$ alkyl or Z is a group of formula (b):

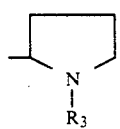

in which $R_3$ is alkyl, alkenyl, cycloalkyl-substituted alkyl or cycloalkenyl-substituted alkyl;
X is hydrogen, amino, methoxy or methyl;
Y is hydrogen, chlorine, cycloalkyl-substituted methylsulphonyl, alkylsulphamoyl or alkylsulphonyl, with the following provisos:
(i) when n is equal to 1 and Z is a group of formula (b) in which $R_3$ is alkyl, then Y cannot be hydrogen or chlorine, and
(ii) when X is hydrogen or amino and Y is alkylsulphamoyl or alkylsulphonyl, then Z cannot be a group of formula (a) as above or a group of formula (b) wherein $R_3$ is alkyl or alkenyl and their pharmacologically acceptable acid addition salts and their optical isomers.

DESCRIPTION OF THE PREFERRED EMBODIMENTS

In the compounds of formula (I), $R_3$ is preferably lower alkyl, more preferably $C_1$-$C_6$ alkyl; lower alkenyl, more preferably $C_2$-$C_6$ alkenyl; cyclo(lower) alkyl-substituted lower alkyl, more preferably ($C_3$-$C_6$ cycloalkyl)-substituted $C_1$-$C_6$ alkyl or cyclo(lower)alkenyl-substituted lower alkyl, more preferably ($C_4$-$C_6$ cycloalkenyl)-substituted $C_1$-$C_6$ alkyl.

In addition, Y is preferably hydrogen; chlorine; cyclo(lower)alkyl-substituted methylsulphonyl, more preferably ($C_3$-$C_6$ cycloalkyl)-substituted methylsulphonyl; (lower)alkylsulphamoyl, more preferably $C_1$-$C_6$ alkylsulphamoyl or (lower)alkylsulphonyl, more preferably $C_1$-$C_6$ alkylsulphonyl.

Pharmacologically acceptable salts of formula I compounds include the non-toxic acid addition salts formed by reacting the carboxamides of the invention with the desired acid. The acid may be an inorganic acid, such as sulfuric, sulfamic, nitric, hydrobromic, hydrochloric, phosphoric and the like, or an organic acid, such as citric, tartaric, lactic, acetic, succinic, fumaric, maleic, benzoic and the like.

Pharmacologically acceptable salts of formula I compounds also include the non-toxic quaternary ammonium salts of the carboxamides of the invention produced by reacting the carboxamides with an aliphatic or aromatic alkylating agent, such as methyl chloride, methyl bromide, dimethyl sulfate, methyl p-toluene sulfonate and the like. In addition, the novel carboxamide compounds include the N-oxides formed by utilizing the conventional agents; see, for example, U.S. Pat. No. 3,838,330, issued Oct. 1, 1974.

When the presence of an asymmetric carbon atom in the formula makes it possible to have optical isomers these also form part of the invention.

The dextrorotatory and levorotatory isomers of the foregoing compounds of the invention are also included within the scope of this invention. Such optically active compounds are conventionally resolved employing a suitably selected optically active acid, which is added to the racemate. The salts thus obtained are separated, for example, by making use of their differences in solubility in an appropriate solvent or by other conventional techniques.

The compounds have therapeutic uses, particularly in activating the central nervous system.

The invention also relates to the preparation of compounds of formula (I).

These compounds may be prepared by reacting an acid of formula (II):

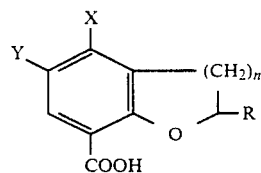

in which R, X, Y and n are defined as above or one of its reactive derivatives, with an amine of formula (III):

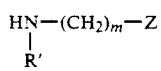

in which m, R' and Z are defined as above.

The compounds of formula (I) in which Z represents a group of formula (b) may also be prepared by reacting an acid of formula (II) as defined above, or one of its reactive derivatives, with a dihaloalkylamine of formula (IV):

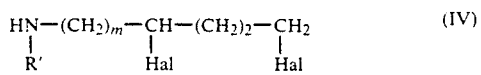

in which Hal represents a halogen atom and R' and m are defined as above, and then reacting the compound obtained, of formula (V):

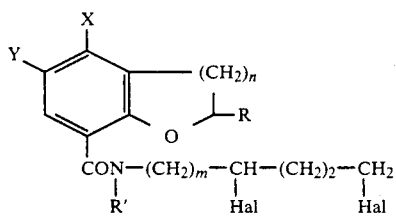

in which R, R', X, Y, m, n and Hal are defined as above, with an amine of formula (VI):

$H_2N-R_3$        (VI)

in which $R_3$ is defined as above.

The reactive derivatives of the acid of formula (II) which are used in the process of the invention include, in particular, acid halides, esters, symmetrical anhydrides and mixed anhydrides.

The reactive derivative of the acid of formula (II) may be used in the amidification reaction, directly after its preparation or after having been isolated from the reaction medium.

The amidification reaction may be carried out in the presence of a solvent such as acetone, methyl ethyl ketone, chloroform and dimethylformamide.

The compounds of the invention may be isolated in the form of bases or converted into acid addition salts by reacting with an inorganic or organic acid.

The optical isomers of compounds of formula (I) may be prepared by the chemical combination of the corresponding racemic compounds, with an optically active acid or by reacting an acid of formula (II) with an optical isomer of the amine of formula (III), or in the case where R is a methyl group, by reacting an amine of formula (III) with an optical isomer of the acid of formula (II).

The following examples illustrate the preparation of the compounds of the invention:

Example 1:
N-(1-Cyclohexenylmethyl-2-pyrrolidinylmethyl)-5-methylsulphamoyl-2-methyl-2,3-dihydrobenzofuran-7-carboxamide.

Step I - Preparation of 5-Chlorosulphonyl-2-methyl-2,3-dihydrobenzofuran-7-carboxylic acid-Intermediate (A)

630 g of chlorosulphonic acid were introduced into a 1-liter round-bottomed flask. The contents were cooled to 0° C. and 160 g of finely ground 2-methyl-2,3-dihydrobenzofuran-7-carboxylic acid were then added in portions, maintaining the temperature between 0° and 5° C. by cooling in an ice bath.

The mixture was stirred for 1 hour at 5° C., stirred for 1 hour at ambient temperature, poured onto ice with stirring at a constant temperature of 0° C. by cooling in an ice bath and introducing ice into the round-bottomed flask. The crystals formed were filtered, washed with water and dried in air.

Weight obtained: 213 g (yield −85.5%).

Step II - Preparation of 5-Methylsulphamoyl-2-methyl-2,3-dihydrobenzofuran-7-carboxylic acid-Intermediate (B)

108 g of a 40% aqueous solution of methylamine and 108 ml of water were added into a 2-liter round-bottomed flask. The contents were cooled to 5° C. and 193 g of 5-chlorosulphonyl-2-methyl-2,3-dihydrobenzofuran-7-carboxylic acid were then added in portions of 10 g, while cooling in an ice and salt bath so as to maintain the temperature at 5° C. After each addition of acid, 14.5 ml of a solution containing 140 ml of 30% sodium hydroxide in 140 ml of water were added.

The solution obtained was diluted, filtered and then acidified with concentrated hydrochloric acid until a color change of Congo red was observed.

The precipitate obtained was drained, washed and dried at 50° C. After recrystallization in methanol, 119 g of acid ( (m.p.=214° C.; yield −63%) were obtained.

Step III - Preparation of 5-Methylsulphamoyl-2-methyl-2,3-dihydro-benzofuran-7-carbonyl chloride-Intermediate (C)

232 g of thionyl chloride and 66 g of 5-methyl-sulphamoyl-2-methyl-2,3-dihydrobenzofuran-7-carboxylic acid were introduced into a 1-liter round-bottomed flask. The flask was heated in a water bath until the contents dissolved and 66 g of the acid were then added and the heating continued until they dissolved. Excess thionyl chloride was removed by distillation under vacuum to constant weight and the residue was then treated with petroleum ether.

The pasty product obtained was strained and dried under vacuum.

Step IV - Preparation of Title product: N-(1-Cyclohexenylmethyl-2-pyrrolidinylmethyl)-5-methyl-sulphamoyl-2-methyl-2,3-dihydrobenzofuran-7-carboxamide 95 g of 1-cyclohexenylmethyl-2-aminomethylpyrrolidine and 380 ml of chloroform were introduced into a 2-liter round-bottomed flask. The contents were cooled to 5° C. and a solution of 142 g of 5-methylsulphamoyl-2-methyl-2,3-dihydrobenzofuran-7-carbonyl chloride in 300 ml of chloroform was poured in dropwise, while maintaining the temperature between 5° and 10° C. with external cooling.

The temperature was then allowed to rise and the reaction medium was then taken up with water. After removing the chloroform, the remaining solution was filtered and made alkaline with 20% ammonia until a color change of phenolphthalein was obtained.

The precipitate, which solidified after the addition of ether, was drained, washed with water and dried at 50° C.

The 170 g of base obtained were dissolved in the heated state in 510 ml of absolute ethanol. The boiling solution was filtered and the crystals formed by cooling were drained, washed with ethanol and dried at 50° C.

101 g of the base were obtained, which were recrystallized in 300 ml of absolute ethanol.

Weight obtained: 86 g (m.p. −155°-156° C.; yield=39%).

Example 2:
N-(1-Cyclohexenylmethyl-2-pyrrolidinylmethyl)-6-methylsulphamoylchroman-8-carboxamide

Step I - Preparation of 6-chlorosulphonylchroman-8-carboxylic acid-Intermediate (D)

930 ml of chlorosulphonic acid were introduced into a 1-liter round-bottomed flask and 165 g of chroman-8-carboxylic acid were then added in small amounts, while maintaining the temperature between 0° C. and 10° C. by cooling. The solution was stirred for 1 hour at 10° C., and then allowed to stand overnight at ambient temperature. It was then poured in small amounts onto ice, while stirring and maintaining the temperature at 0° C. by cooling externally and by introducing ice into the flask.

The crystals formed were drained, washed with water and air-dried.

Weight obtained = 254 g (yield −99%).

Step II - Preparation of 6-Methylsulphamoylchroman-8-carboxylic acid-Intermediate (E)

207 g of a 40% aqueous solution of methylamine were introduced into a 1-liter round-bottomed flask and 123 g of finely ground 6-chlorosulphonylchroman-8-carboxylic acid were then added in portions, while maintaining the temperature between 0° C. and 5° C., by cooling.

The mixture was maintained at 5° C. for 45 minutes and then the temperature was allowed to rise. The solution obtained was diluted with 1 liter of water, filtered and then acidified with 125 ml of concentrated hydrochloric acid. The acid obtained was drained, washed with water and dried at 50° C.

Weight obtained = 107 g (m.p. = 204° C.; yield −90%).

Preparation of Title compound N-(1-Cyclohexenylmethyl-2-pyrrolidinylmethyl)-6-methylsulphamoylchroman-8-carboxamide 76 g of 6-methylsulphamoylchroman-8-carboxylic acid, 200 ml of chloroform and 28.5 g of triethylamine were introduced into a 1-liter round-bottomed flask. The contents were cooled to 0° C. and 30.5 g of ethyl chloroformate were then added dropwise while maintaining the temperature between 0° and 5° C., by cooling in an ice bath. The mixture was stirred at this temperature for 30 minutes and a solution of 55.5 g of 1-cyclohexenylmethyl-2-aminomethylpyrrolidine in 50 ml of chloroform was added dropwise, between 0° and 5° C.

The temperature was then allowed to rise and the reaction mixture allowed to stand overnight. The solution obtained was taken up with water and the chloroform was distilled off. The hydrochloride crystals were redissolved in the heated state after adding 1.8 liter of water. The boiling solution was filtered and then made alkaline by adding 30% sodium hydroxide until a color change of phenolphthalein was observed. The oil formed was cooled, decanted and extracted with methylene chloride. The solution containing methylene chloride was dried over potassium carbonate and the methylene chloride was then distilled off. The distillation, towards the end, was carried out under vacuum, until a constant weight was obtained.

The 126 g of the product obtained were then redissolved in the heated state in 250 ml of absolute ethanol. The crystals formed by cooling were drained, washed with ethanol and dried. 99.5 g of a product were obtained, which recrystallized in 200 ml of ethanol.

Weight obtained: 90.5 g (m.p. = 144.5° C.-145.5° C.; yield −72%)

Example 3:
N-(1-Cyclohexenylmethyl-2-pyrrolidinylmethyl)-5-cyclopropylmethylsulphonyl-2-methyl-2,3-dihydrobenzofuran-7-carboxamide methanesulphonate

Step I - Preparation of 5-Mercapto-2-methyl-2,3-dihydrobenzofuran-7-carboxylic acid-Intermediate (F)

216 g of 5-chlorosulphonyl-2-methyl-2,3,-dihydrobenzofuran-7-carboxylic acid, 585 ml of acetic acid and 348 g of tin were introduced into a 6-liter round-bottomed flask and 1560 ml of concentrated hydrochloric acid (d =1.18) were then added dropwise, while maintaining the temperature between 45° and 55° C. The contents were then heated for 2 hours at 55°–60° C. until the tin was completely dissolved, and the solution which was poured into 12 liters of water was then filtered. The crystals formed were drained, washed with water and dried at 40° C.

Weight obtained: 130.5 g (m.w. = 225); (m.p. = 158° C.) (yield = 79.5%).

Step II - Preparation of 5-Cyclopropylmethylthio-2-methyl-2,3-dihydrobenzofuran-7-carboxylic acid-Intermediate (G)

73 g of potassium hydroxide were dissolved in 84 ml of water in a 2-liter round-bottomed flask and 387 ml of absolute ethanol and 130.5 g of 5-mercapto-2-methyl-2,3-dihydrobenzofuran-7-carboxylic acid were then added. 86 g of cyclopropylmethyl bromide were then quickly poured in and the contents were heated under reflux for 1 hour. After adding water, the contents were filtered and the solution was acidified by adding concentrated hydrochloric acid until a color change of Congo red was observed. The precipitate formed was drained, washed with water and dried at 40° C.

Weight obtained = 133 g (m.p. −90° C.; yield = 87%).

Step III - Preparation of 5-Cyclopropylmethylsulphonyl-2-methyl-2,3-dihydrobenzofuran-7-carboxylic acid-Intermediate (H)

133 g of 5-cyclopropylmethylthio-2-methyl-2,3-dihydrobenzofuran-7-carboxylic acid were dissolved in 735 ml of acetic acid in a 2-liter round-bottomed flask and 315 ml of 107.5 volume hydrogen peroxide were then added. The temperature rose from 20° C. to 40° C.

The contents were then heated under reflux for 5 hours, the major part of acetic acid was distilled off and the residue was taken up with 3 liters of water.

The crystals formed were drained, washed with water and dried at 40° C.

Weight obtained: 133.5 g (m.p. = 178° C.; yield = 89%).

Step IV - Preparation of N-(1-Cyclohexenylmethyl-2-pyrrolidinyl-methyl)-5-cyclopropylmethylsulphonyl-2-methyl-2,3-dihydrobenzofuran-7-carboxamide (Compound of the Invention)

97 g of 5-cyclopropylmethylsulphonyl-2-methyl-2,3-dihydrobenzofuran-7-carboxylic acid, 350 ml of chloroform and 34 g of triethylamine were introduced into a 1-liter round-bottomed flask. The solution was cooled to 0° C. and 36 g of ethyl chloroformate were then added dropwise, while maintaining the temperature between 0° C. and 5° C. The contents were then stirred for 1 hour between 0° C. and 5° C. and 67 g of 1-cyclohexenylmethyl-2-aminomethylpyrrolidine were then poured in dropwise, between 5° C. and 10° C. The mixture was stirred for 1 hour, between 5° and 10° C. and the temperature was then allowed to rise. The solution obtained was taken up with 2 liters of water. Acetic acid was added until a pH of 4 was obtained and the chloroform was distilled off. The solution remaining was filtered and then made alkaline with 30% sodium hydroxide until a color change of phenolphthalein was observed. The oil formed was decanted and extracted with ether and the solution containing ether was then dried over potassium carbonate. The ether was distilled off, the distillation towards the end being carried out under vacuum, until a constant weight was obtained.

Weight obtained = 146 g (yield = 94%).

Preparation of Title compound:
N-(1-Cyclohexenylmethyl-2-pyrrolidinylmethyl)-5-cyclopropylmethylsulphonyl-2-methyl-2,3-dihydrobenzofuran-7-carboxamide methane sulphonate 141 g of N-(1-cyclohexenylmethyl-2-pyrrolidinylmethyl)-5-cyclopropylmethylsulphonyl-2-methyl-2,3-dihydrobenzofuran-7-carboxamide were dissolved in 340 ml of ethyl acetate and 29 g of methanesulphonic acid were then added.

The crystals formed were drained, washed with ethyl acetate and dried at 40° C.

133 g of product were obtained, which were redissolved in the heated state in 400 ml of isopropyl alcohol.

The boiling solution was filtered with charcoal. The crystals formed on cooling were drained, washed with isopropyl alcohol and dried at 40° C.

The product obtained was left exposed to the air until its weight was constant.

120 g of a product containing 1 mole of water (m.p. = 126° C.; yield = 68%) were obtained.

Example 4:
N-(1-Ethyl-2-pyrrolidinylmethyl)-6-cyclopropyl methylsulphonylchroman-8-carboxamide Step I - Preparation of
6-Mercaptochroman-8-carboxylic acid-Intermediate (I)

238 g of 6-chlorosulphonylchroman-8-carboxylic acid and 645 ml of acetic acid were introduced into a 6-liter round-bottomed flask. The mixture was heated to 80° C. and 384 g of tin was added and the mixture was then cooled to 50° C. 1720 ml of hydrochloric acid (d = 1.18) were then poured in dropwise, while maintaining the temperature between 55° and 60° C. first by cooling in an ice bath and then by heating in a water bath. Heating was then continued for 3 hours at 60° C. and the solution was poured into 6 liters of water. The precipitate formed was drained, washed with 1 liter of dilute hydrochloric acid followed by water and then air-dried.

Weight obtained: 168 g (m.p. = 130°–133° C.; yield −93%).

Step II - Preparation of
6-Cyclopropylmethylthio-chroman-8-carboxylic acid-Intermediate (J).

90 g of potassium hydroxide were dissolved in 90 ml of water in a 3-liter round-bottomed flask and 900 ml of ethanol and 137 g of 6-mercaptochroman-8-carboxylic acid were then added. 162 g of 90% cyclopropylmethyl tosylate were then poured in dropwise.

The mixture was heated under reflux for 3 hours and a part of the alcohol was distilled off and the residue taken up with water.

The solution obtained was filtered with charcoal and then acidified with concentrated hydrochloric acid.

The crystals formed were drained, washed with water and air-dried.

Weight obtained = 177 g (m.p. = 85° C.; m.w. = 295; yield = 91% on a dry-weight basis).

Step III - Preparation of
6-Cyclopropylmethylsulphonylchroman-8-carboxylic acid-Intermediate (K)

177 g of 6-cyclopropylmethylthiochroman-8-carboxylic acid, 780 ml of acetic acid and 366 ml of 110 volume hydrogen peroxide were introduced into a 3-liter round-bottomed flask. The contents were then heated in a water bath for 5 hours and the solution was filtered with charcoal and a part of the acetic acid was distilled off.

The residue was taken up with water and the solid obtained was drained, washed with water and dried at 40°–50° C.

Weight obtained = 146 g (yield = 82%).

Preparation of Title compound:
N-(1-Ethyl-2-pyrrolidinylmethyl)-6-cyclopropylmethyl-sulphonylchroman-8-carboxamide)

100 g of 6-cyclopropylmethylsulphonylchroman-8-carboxylic acid, 500 ml of chloroform and 34 g of triethylamine were introduced into a 2-liter round-bottomed flask. The contents were cooled to 0° C. and 37 g of ethyl chloroformate were added dropwise, while maintaining the temperature between 0° and 5° C. by cooling. The mixture was stirred for 30 minutes at 5° C., and 47.5 g of 1-ethyl-2-aminomethylpyrrolidine were then poured in dropwise, while maintaining the temperature between 5° C. and 10° C. The contents were stirred for 1 hour at 10° C. and the temperature was then allowed to rise.

The chloroform was distilled off under a slight vacuum and the residue was taken up with water and hydrochloric acid.

The solution obtained was filtered with charcoal and then made alkaline with 20% ammonia until a color change of phenolphthalein was observed.

The solid formed was drained, washed with water and dried at 40° C.

110 g of product were obtained, which were dissolved in 210 ml of isopropanol. A solution of 9.8 g of hydrogen chloride gas in 25 ml of isopropanol was then added until the color change of methyl red was observed. The hydrochloride formed was drained, washed with isopropanol and dried and then dissolved in 450 ml of water.

The solution was filtered with charcoal and made alkaline with 20% ammonia until a color change of phenolphthalein was observed.

87 g of a beige product were obtained (m.p. = 104°–105° C.), which were purified once again.

The 87 g of base were dissolved in 160 ml of isopropanol and a solution of 7.8 g of hydrogen chloride gas in 20 ml of isopropanol was added until a color change of methyl red was observed. The crystals formed were drained, washed with isopropanol and dried at 40° C.

91 g of hydrochloride were obtained, which were dissolved in 220 ml of water. The solution was filtered with charcoal and then made alkaline with 20% ammonia until a color change of phenolphthalein was observed. The crystals formed were drained, washed with water and dried at 40° C.

Weight obtained: 82.5 g (m.p.=106°-106.5° C.; yield=60%).

Example 5:
N-(1-Allyl-2-pyrrolidinylmethyl)-6-cyclopropyl methylsulphonylchroman-8-carboxamide.

102 g of 6-cyclopropylmethylsulphonylchroman-8-carboxylic acid, 350 ml of acetone and 35 g of triethylamine were introduced into a 1-liter round bottomed flask. The contents were cooled to 0° C. and 37 g of ethyl chloroformate were then added dropwise. The contents were stirred for 20 minutes between 0° and 5° C. and 48 g of 1-allyl-2-aminomethylpyrrolidine were then poured in dropwise, while maintaining the temperature between 5° and 10° C. The temperature was then allowed to rise and the mixture was stirred for 2 hours. The precipitate of triethylamine hydrochloride was drained and the acetone was distilled off in a water bath, the distillation towards the end being carried out under vacuum, until a constant weight was obtained. The residue was taken up with water and acidified with acetic acid until the pH was 4. The solution obtained was filtered with charcoal and then made alkaline with 20% ammonia until a color change of phenolphthalein was observed. The oil formed was decanted and extracted with methylene chloride and the solution containing methylene chloride was dried over potassium carbonate. The methylene chloride was then distilled off, the distillation towards the end being carried out under vacuum, until a constant weight was obtained.

134 g of an oily product were obtained, which were taken up with 300 ml of ether and dried in air and then at 50° C.

Weight obtained: 124 g (m.p. −100° C.; yield=86%).

120 g of base were dissolved in 240 ml of absolute ethanol and a solution of 10.5 g of hydrogen chloride gas in 50 ml of absolute ethanol was then added until a color change of methyl red was observed. The hydrochloride crystallized on cooling was drained at about 10° C., washed with ethanol followed by with water and dried in air and then at 45° C.

102 g of hydrochloride were obtained which were dissolved in water. Charcoal was added and left in contact for one hour and the mixture was then filtered and the solution was made alkaline with 20% of ammonia and ether was added in order to promote crystallization. The crystals formed were drained, washed with water and dried in air and then in an oven at 50° C.

The 90 g of base obtained were recrystallized in 180 ml of 95% ethanol. The crystals were drained, washed and dried at 50° C. and then at 60°-65° C. for one day.

Weight obtained: 78.5 g (m.p.=114° C.; purification yield =65%; total yield=56%).

Example 6:
N-(1-Cyclopropylmethyl-2-pyrrolidinylmethyl)-6-cyclopropylmethylsulphonylchroman-8-carboxamide.

63 g of 6-cyclopropylmethylsulphonylchroman-8-carboxylic acid, 250 ml of chloroform and 21.5 g of triethylamine were introduced into a 1-liter round bottomed flask. The contents were cooled to 5° C. and 23 g of ethyl chloroformate were added dropwise, while maintaining the temperature between 0° and 5° C. The contents were then stirred for 30 minutes at 5° C. and 35.5 g of 1-cyclopropylmethyl-2-aminomethylpyrrolidine were then poured in dropwise, between 5° and 10° C. The contents were then stirred for 1 hour at 10° C. and for 2 hours while allowing the temperature to rise. The major part of the chloroform was distilled off under a slight vacuum and the residue was taken up with water and hydrochloric acid. The remaining chloroform was removed by carrying over with water diluted to obtain 600 ml of solution and then made alkaline with 20% ammonia until a color change of phenolphthalein was observed. The oil formed was crystallized after addition of ether.

The product obtained was drained, washed with water and air-dried. Weight obtained: 89 g (yield=97%).

The 89 g of base were dissolved in 210 ml of absolute ethanol and 24 g of 85% phosphoric acid. The crystals formed were drained, washed and dried.

87 g of phosphate were obtained, which were dissolved in 800 ml of water containing a small amount of sodium metabisulphite. The solution obtained was filtered with charcoal and then made alkaline with 20% ammonia in the presence of a small amount of ether.

The crystals formed were drained, washed with water and dried at 30° C.

The 69 g of base obtained were recrystallized in 140 ml of isopropanol. After draining and drying, 55 g of product were obtained, which were redissolved in the heated state in 110 ml of isopropanol. The boiling solution was filtered with charcoal. The base crystallized on cooling, was drained, washed with isopropanol and dried at 30° C.

Weight obtained: 43.5 g (m.p.=95°-95.5° C.; purification yield: 50%; total yield=48%).

Example 7:
N-(1-Cyclopropylmethyl-2-pyrrolidinylmethyl)-6-ethylsulphonylchroman-8-carboxamide hydrochloride.

Step I - Preparation of
6-Ethylsulphonylchroman-8-carboxylic acid-Intermediate (L)

461 ml of water, 100 g of anhydrous sodium sulphite and 134 g of sodium bicarbonate were introduced into a 3-liter round-bottomed flask. The contents were heated to 70° C., while stirring and 147 g of 6-chlorosulphonylchroman-8-carboxylic acid were then introduced in small amounts, between 70° and 80° C. The temperature was then maintained between 70° and 80° C. for 2 hours The solution was cooled to 20° C. and 106 ml of 30% sodium hydroxide, 530 ml of ethanol and 249 g of ethyl iodide were then added. The mixture was heated to reflux temperature which increased gradually during the reaction from 60° C. initially to 82° C. after 18 to 20 hours of heating. After cooling, the reaction mixture was taken up with water, the solution was filtered with charcoal and acidified with concentrated hydrochloric acid until a color change of Congo red was observed. The precipitate formed was drained, washed with water and dried at 40° C.

Weight obtained=121 g (m.p.=156°-157° C.; yield=84.5%).

Step II - Preparation of N-(1-Cyclopropylmethyl-2-pyrrolidinyl-methyl)-6-ethyl-sulphonylchroman-8-carboxamide (Compound of the Invention)

80.5 g of 6-ethylsulphonylchroman-8-carboxylic acid, 440 ml of acetone and 30 g of triethylamine were introduced into a 1-liter round-bottomed flask. The contents were cooled to 0° C. and 32.5 g of ethyl chloroformate were introduced dropwise, while maintaining the temperature between 0° and 5° C.

The mixture was stirred for 30 minutes at 5° C. and 46 g of 1-cyclopropylmethyl-2-aminomethylpyrrolidine were then added dropwise, with cooling. The contents were stirred for one hour while allowing the temperature to rise and the triethylamine hydrochloride was then drained. The acetone was distilled off, the distillation towards the end being carried out under vacuum, until a constant weight was obtained and the residue was dissolved in water and in hydrochloric acid. The solution obtained was filtered with charcoal and then made alkaline with 20% ammonia until a color change of phenol-phthalein was observed.

The oil formed was decanted and extracted with methylene chloride and the solution containing methylene chloride was dried over potassium carbonate. The methylene chloride was distilled off, the distillation towards the end being carried out under vacuum, until a constant weight was obtained.

Weight obtained: 115 g (yield=95%).

Step III - Preparation of Title compound: N-(1-Cyclopropylmethyl-2-pyrrolidinyl-methyl)-6-ethyl-sulphonylchroman-8-carboxamide hydrochloride 130 g of N-(1-cyclopropylmethyl-2-pyrrolidinylmethyl)-6-ethylsulphonylchroman-8-carboxamide were dissolved in 230 ml of ethanol and a solution of 12 g of hydrogen chloride gas in 20 ml of absolute ethanol was then added until a color change of methyl red was observed.

The crystals which formed were drained, washed with absolute ethanol and dried in air and then at 60° C.

The 106 g of hydrochloride obtained were redissolved in the heated state in 212 ml of absolute ethanol. The boiling solution was filtered with charcoal. After cooling, the crystals formed were drained, washed with absolute ethanol and with ether and dried in air and then at 60° C.

Weight obtained: 96 g (m.p.=182°–183° C.; yield=68%).

Example 8: N-(1-Cyclopropylmethyl-2-pyrrolidinylmethyl)-5-amino-6-ethylsulphonylchroman-8-carboxamide.

Step I - Preparation of Methyl 4-bromosalicylate-Intermediate (M)

460 g of 66% hydrobromic acid, 820 ml of water and 209 g of methyl 4-aminosalicylate were introduced into a 4-liter round-bottomed flask. The suspension obtained was cooled to 0° C. and a solution of 92 g of sodium nitrite in 90 ml of water were then added dropwise, while maintaining the temperature between 0° and 5° C.

The mixture was then stirred for 1 hour.

498 g of 66% hydrobromic acid, 185 ml of water and 125 g of cuprous bromide were introduced into a 6-liter round-bottomed flask. The temperature rose to 40° C. The solution obtained previously was then poured in dropwise. The temperature remained between 45° and 50° C. by itself.

The brominated ester separated into an oily layer which became solid on cooling.

The solid obtained was drained, washed with water and with 10% hydrochloric acid and then redissolved in ether. The solution containing ether was then washed with 10% hydrochloric acid until the disappearance of $Cu^{2+}$ ions and then washed with water and dried over sodium sulphate. After removing the ether, the remaining product was distilled under vacuum.

The product distilling between 142° and 158° C. at 14 mm Hg, which is compatible with the expected structure, was collected.

236 g of product which crystallized was obtained (yield=82%; m.p.=38° C.

Step II - Preparation of Methyl 2-allyloxy-4-bromobenzoate-Intermediate (N)

139 g of ground potassium carbonate, 470 ml of acetonitrile, 16 g of benzyltributylammonium chloride and 136 g of allyl bromide were introduced into a 3-liter round-bottomed flask and 236 g of ground methyl 4-bromosalicylate were added in small amounts. The contents were heated under reflux with vigorous stirring, for 5 hours and then a part of the acetonitrile was distilled off under slight vacuum and the residue was taken up with water. A precipitate of methyl 2-allyloxy-4-bromobenzoate was obtained, which was drained, washed with water and air-dried.

Weight obtained: 280 g (m.p.=62° C.).

Step III - Preparation of Methyl 2-hydroxy-3-allyl-4-bromobenzoate-Intermediate (O)

93 g of methyl 2-allyloxy-4-bromobenzoate were introduced into a 500 ml round-bottomed flask and the flask was then heated gently until the product melted. The product was heated to its boiling point and heating was then discontinued, the reaction proceeding by itself with evolution of heat.

The same operations were repeated twice, with 93 g of the product. The products of the three trials were combined and distilled. The fraction distilling at 105°–115° C. at 0.1–0.3 mm Hg, was collected.

Weight obtained: 254 g (yield=91%).

Step IV - Preparation of Methyl 2-acetoxy-3-allyl-4-bromobenzoate-Intermediate (P)

254 g of methyl 2-hydroxy-3-allyl-4-bromobenzoate and 191 g of acetic anhydride were introduced into a 1-liter round-bottomed flask and 2 ml of sulphuric acid were then added.

The contents were then heated for 3 hours in a water bath and the solution obtained was then poured into ice-cold water.

The crystallized product which formed was drained, washed with water and then dried at ambient temperature and then in a fan-assisted oven.

Weight obtained: 272 g (yield=93%; m.p.=59° C.).

Step V - Preparation of Methyl 2-acetoxy-3-(gamma-bromopropyl)-4-bromobenzoate-Intermediate (Q)

282 g of methyl 2-acetoxy-3-allyl--bromobenzoate, 850 ml of carbon tetrachloride and 7 g of benzoyl peroxide were introduced into a 3-liter round-bottomed flask and the solution obtained was then cooled to −5° C. A stream of hydrogen bromide gas was then passed through until the weight of the reaction mixture was approximately 110 g. The temperature was maintained between −5° C. and 0° C. for the entire period of absorption.

The contents were then stirred between −5° C. and 0° C., for 2 hours and the temperature was allowed to rise.

The solution obtained was taken up with 3 liters of water. The organic phase was decanted and the aqueous layer extracted with carbon tetrachloride.

The organic layers were combined, washed to neutrality with an ice-cold, 4% sodium bicarbonate solution and then dried over sodium sulphate.

The carbon tetrachloride was then distilled off, the distillation towards the end being carried out under vacuum, until a constant weight was obtained. The product remaining was redissolved in the heated state in 450 ml of isopropanol.

The crystals obtained after cooling were drained, washed with isopropanol and dried at 20° C. in a fan-assisted oven.

Weight obtained: 256 g (yield=72% m.p.=83° C.).

Step VI - Preparation of 5-Bromochroman-8-carboxylic acid-Intermediate (R)

326 g of methyl 2-acetoxy-3-(gamma-bromopropyl)-4-bromobenzoate and 1655 ml of 10% sodium hydroxide were introduced into a 4-liter round-bottomed flask and the contents were heated under reflux for 1 hour.

The solution was taken up with boiling water and concentrated hydrochloric acid was then added until a color change of Congo red was observed.

After cooling, the product obtained was drained, washed with water and dried at 50° C.

Weight obtained: 210 g (yield=99%; m.p.=167° C.

Step VII - Preparation of 5-Bromo-6-chlorosulphonylchroman-8- carboxylic acid-Intermediate (S)

817 ml of chlorosulphonic acid were introduced into a 2-liter round-bottomed flask and 210 g of 5-bromochroman-8-carboxylic acid were then added in small amounts. The temperature rose to 40° C.

When the introduction was complete, the contents were heated for 4 hours with a water bath, at 40° C. The solution obtained was poured onto ice, with stirring and maintaining the temperature at 0° C. with external cooling. The precipitate formed was drained, washed and air-dried.

Weight obtained: 255 g (yield=88%).

Step VIII - Preparation of 5-Bromo-6-ethylsulphonylchroman-8-carboxylic acid-Intermediate (T)

765 ml of water, 136 g of anhydrous sodium sulphite and 181 g of sodium bicarbonate were introduced into a 6-liter round-bottomed flask. The contents were heated, with stirring, to 70° C. and 255 g of 5-bromo-6-chlorosulphonylchroman-8-carboxylic acid were then added in small amounts, between 70° and 80° C. The contents were then heated for 2 hours, between 70° and 80° C.

After cooling to 20° C., 890 ml of ethanol, 144 ml of 30% sodium hydroxide and 314 g of ethyl iodide were added and the contents were heated under reflux, while maintaining the medium alkaline by adding sodium hydroxide. During the reaction, the reflux temperature rose slowly from 60° to 82° C.

A part of the alcohol was then distilled and the residue taken up with water. The solution obtained was filtered with charcoal and then acidified by adding concentrated hydrochloric acid until a color change of Congo red was observed. The precipitate formed was drained, washed with water and then dried in an oven at 50° C. and recrystallized in 450 ml of absolute ethanol.

Weight obtained: 223 g (yield −89%; m.p.=177° C.

Step IX - Preparation of 5-Amino-6-ethylsulphonylchroman-8-carboxylic acid-Intermediate (U)

118 g of 5-bromo-6-ethylsulphonylchroman-8-carboxylic acid, 460 ml of 34% ammonia, 5 g of powdered copper and 4 g of cuprous chloride were introduced into a 1-liter autoclave and the contents were then heated between 115° and 120° C., for 10 to 12 hours, with stirring.

After cooling, the solution obtained was filtered with charcoal and then acidified with acetic acid until the pH was 4.

The precipitate formed was drained, washed with water and dried at 40° C.

The 63.5 g of product obtained were suspended in 90 ml of boiling 2-methoxyethanol.

This suspension was cooled, drained, washed with 2-methoxyethanol and dried at 50° C.

Weight obtained: 58 g (yield=60%; m.p.=260° C.).

Step X - Preparation of Title compound: N-(1-Cyclopropylmethyl-2-pyrrolidinyl-methyl)-5-amino-6-ethylsulphonylchroman-8-carboxamide 44 g of 5-amino-6-ethylsulphonylchroman-8-carboxylic acid, 170 ml of chloroform and 15.5 g of triethylamine were introduced into a 500 ml round-bottomed flask and the contents were then cooled to 5° C.

17 g of ethyl chloroformate were then added dropwise between 5° and 10° C. The contents were stirred for 30 minutes at 10° C. and 26 g of 1-cyclopropylmethyl-2-aminomethylpyrrolidine were then poured in dropwise, between 10° and 15° C.

The contents were stirred at 10° C. for 1 hour, and the temperature was then allowed to rise. The chloroform was then distilled off and the residue was taken up with water and with acetic acid sufficient to bring the pH to 4.

The solution obtained was filtered with charcoal and made alkaline by adding 20% ammonia until a color change of phenolphthalein was observed. The 60 g of product obtained were drained, washed with water and dried at 50° C. and then redissolved in the heated state in 116 ml of absolute ethanol. The boiling solution was filtered with charcoal. Since crystallization is very rapid, the base crystallized in the filter.

After concentration of the alcoholic solutions, the entire amount of the product was taken up with acidified water.

The solution was filtered and made alkaline by adding ammonia until a color change of phenolphthalein was observed.

The product obtained was drained, washed with water, dried at 50° C. and recrystallized in 112 ml of methanol.

Weight obtained: 46 g (yield=71%; m.p.=151°-152° C.).

Example 9:
N-(1-Cyclopropylmethyl-2-pyrrolidinylmethyl)-5-ethylsulphonyl-2-methyl-2,3-dihydrobenzofuran-7-carboxamide hydrochloride

Step I - Preparation of 5-Ethylsulphonyl-2-methyl-2,3-dihydrobenzofuran-7-carboxylic acid-Intermediate (V)

147 g of sodium sulphite, 196 g of sodium bicarbonate and 870 ml of water were introduced into a 4-liter round-bottomed flask. The contents were heated to 80° C. and 215 g of 5-chlorosulphonyl-2-methyl-2,3-dihydrobenzofuran-7-carboxylic acid were then added in small amounts, between 70° and 80° C. The contents were then heated for 2 hours at 80° C. until gas evolution was complete.

The contents were cooled to 20° C. and 800 ml of ethanol, 240 ml of 30% sodium hydroxide and 364 g of ethyl iodide were then added and the mixture was heated under reflux, the losses of ethyl iodide being replenished.

In 54 hours and 30 minutes of elapsed time, 86 g of ethyl iodide were added and the temperature rose from 60° C. to 82° C.

After distilling off part of the alcohol, the residue was taken up with 1.6 liters of water. The solution obtained was filtered with charcoal and then acidified with concentrated hydrochloric acid until a color change of Congo red was observed.

The precipitate formed was drained, washed with water, dried at 50° C. and then redissolved in 900 ml of water and sodium bicarbonate. The solution was filtered with charcoal and acidified with concentrated hydrochloric acid until a color change of Congo red was observed.

The precipitate was drained, washed with water and dried at 50° C.

Weight obtained: 172 g (m.p.=191° C.; yield=82%).

Step II - Preparation of N-(1-Cyclopropylmethyl-2-pyrrolidinylmethyl)-5-ethylsulphonyl-2-methyl-2,3-dihydrobenzofuran-7-carboxamide (A Compound of the Invention 81 g of 5-ethylsulphonyl-2-methyl-2,3-dihydrobenzofuran-7-carboxylic acid, 300 ml of chloroform and 30 g of triethylamine were introduced into a 1-liter round-bottomed flask. The contents were cooled to 0° C. and 32 g of ethyl chloroformate were then added dropwise, while maintaining the temperature between 0° and 5° C. The contents were stirred for 2 hours and 46.5 g of 1-cyclopropylmethyl-2-aminomethylpyrrolidine were then added dropwise, while maintaining the temperature between 5° and 10° C.

The temperature was then allowed to rise, the solution was then taken up with 1600 ml of water and acidified to a pH of 4 with acetic acid. The chloroform was distilled off with charcoal and made alkaline with 20% ammonia until a color change of phenolphthalein was observed.

The oil formed was decanted and extracted with ether. The solution obtained was dried over potassium carbonate and the ether was then distilled off, the distillation towards the and being carried out under vacuum, until a constant weight was obtained.

Weight obtained=104 g (yield=85%).

Step III - Preparation of Title compound: N-(1-Cyclopropylmethyl-2-pyrrolidinylmethyl)-5-ethylsulphonyl-2-methyl-2,3-dihydrobenzofuran-7-carboxamide hydrochloride 104 g of the base were dissolved in 370 ml of ethyl acetate and a solution of 9.5 g of hydrogen chloride gas in 70 ml of ethyl acetate was then added.

The hydrochloride precipitate was then drained, washed with 50 ml of ethyl acetate and then with ether and dried in air and then at 40° C.

The 104 g of hydrochloride obtained were dissolved in 520 ml of water and the solution was then filtered with charcoal and made alkaline with 20% ammonia until a color change of phenolphthalein was observed.

The oil formed was decanted and extracted with ether. The solution obtained was dried over potassium carbonate and the ether was then distilled off, the distillation towards the end being carried out under vacuum, until a constant weight was obtained.

The 91 g of base obtained were dissolved in 320 ml of ethyl acetate and a solution of 8 g of hydrogen chloride gas in 50 ml of ethyl acetate was then added.

The precipitate formed was drained, washed with ethyl acetate and then with ether and dried in air and then at 40° C.

Weight obtained: 96 g of hydrated product (containing half a mole of water). (M.p.=137°-138° C.; yield=83%).

Example 10:
N-(1-Ethyl-2-pyrrolidinylmethyl)chroman-8-carboxamide fumarate

Step I - Preparation of N-(1-Ethyl-2-pyrrolidinylmethyl)chroman-8-carboxamide (Compound of this Invention)

46 g of chroman-8-carboxylic acid, 188 ml of chloroform and 26 g of triethylamine were introduced into a 1-liter round-bottomed flask. The contents were cooled to 0° C. and 28 g of ethyl chloroformate were then added in small amounts, between 0° and 5° C. The contents were stirred for 30 minutes at 5° C. and 36 g of 1-ethyl-2-aminomethylpyrrolidine were then poured in dropwise, between 5° and 10° C. The contents were then stirred for 1 hour at 10° C. and the temperature was then allowed to rise. The chloroform was distilled off under slight vacuum, the residue was taken up with water and acetic acid was added until a pH of 4 was obtained. The solution obtained was filtered with charcoal and then made alkaline with 20% ammonia until a color change of phenolphthalein was observed.

The oil formed was decanted and extracted with methylene chloride. The solution obtained was washed with water, dried over potassium carbonate and the methylene chloride was then distilled off, the distillation towards the end being carried out under vacuum, until a constant weight was obtained.

Weight obtained: 76.5 g.

Step II - Preparation of Title compound: N-(1-Ethyl-2-pyrrolidinylmethyl)chroman-8-carboxamide fumarate 76 g of base were dissolved in the heated state in 200 ml of isopropanol and 30 g of fumaric acid.

The fumarate crystals formed after reaction and cooling were drained, washed with isopropanol and dried at 40° C.

74 g of fumarate were obtained, which were redissolved in the heated state in 148 ml of absolute ethanol.

The boiling solution was filtered with charcoal and then cooled. The crystals formed were drained, washed with ethanol, dried at 40° C. and then recrystallized in 124 ml of isopropanol. 56 g of fumarate were obtained, which were dissolved in 600 ml of water.

The solution was filtered with charcoal and then made alkaline with 20% ammonia until a color change of phenolphthalein was observed. The oil formed was decanted and extracted with ether. The solution was dried over potassium carbonate and the ether was then distilled off, the distillation towards the and being carried out under vacuum, until a constant weight was obtained.

38 g of base were obtained, which were dissolved in 103 ml of absolute ethanol and 15 g of fumaric acid. The crystals formed on cooling were drained, washed with ethanol and then dried at 40° C. 53 g of fumarate were obtained, which were recrystallized in 100 ml of absolute ethanol. After cooling, draining and washing, the product was dried under normal pressure and then under vacuum at 40° C.

Weight obtained; 44 g (m.p.=122°–123° C.; yield=42%).

Example 11:
N-(1-Cyclohexenylmethyl-2-pyrrolidinylmethyl)-6-ethylsulphonylchroman-8-carboxamide.

· Step I - Preparation of
N-(2,5-Dichloropentyl)-6-ethylsulphonylchroman-8-carboxamide-Intermediate (W)

75 g of 6-ethylsulphonylchroman-8-carboxylic acid, 280 ml of chloroform and 28 g of triethylamine were introduced into a 1-liter round-bottomed flask. The contents were cooled to 0° C. and 30 g of ethyl chloroformate were then added dropwise, while maintaining the temperature between 0° C. and 5° C. The mixture was then stirred for 30 minutes between 0° C. and 5° C.

54 g of 2,5-dichloropentylamine hydrochloride, 280 ml of chloroform and 28 g of triethylamine were introduced into a 2-liter round-bottomed flask and the solution prepared previously was then poured in dropwise. The temperature rose to 27° C. The solution was then taken up with water. The chloroform layer was decanted, dried over sodium sulphate and the chloroform was then distilled off, the distillation towards the end being carried out under vacuum, until a constant weight was obtained.

Weight obtained: 107 g (yield=94%).

Step II - Preparation of Title compound:
N-(1-Cyclohexenylmethyl-2-pyrrolidinylmethyl)-6-ethylsulphonylchroman-8-carboxamide 107 g of finely ground N-(2,5,-dichloropentyl)-6-ethylsulphonylchroman-8-carboxamide and 203.5 g of 1-cyclohexenylmethylamine were introduced into a 1-liter round-bottomed flask. The contents were heated to 60° C. for 2 hours and the solution was then left in an oven at 60° C. for 48 hours. After adding water and 30 ml of 30% sodium hydroxide, the excess amine was distilled off. The mixture was cooled and the precipitate was then extracted with ether. The crystals formed were drained, washed with ether an air-dried.

47 g of product were obtained.

Thereafter, the solutions containing ether were evaporated and the residue was taken up with methylene chloride. The solution was dried over potassium carbonate and the methylene chloride was distilled off, the distillation towards the end being carried out under vacuum, until a constant weight was obtained.

The residue was taken up with ether and the crystals formed were then drained, washed and air-dried.

A further 21 g of the product were obtained.

The 68 g of product were redissolved in the heated state in 136 ml of isopropanol. The boiling solution was filtered with charcoal and then cooled. The crystals formed were drained, washed with isopropanol and then with ether and dried in air and then at 35° C.

Weight obtained: 57 g (m.p.=91° C.; yield=49%)

Example 12:
N-(1-Ethyl-2-pyrrolidinylmethyl)-5-cyclopropylmethylsulphonyl-2-methyl-2,3-dihydrobenzofuran-7-carboxamide.

68 g of 5-cyclopropylmethylsulphonyl-2-methyl-2,3-dihydrobenzofuran-7-carboxylic acid, 500 ml of chloroform and 23 g of triethylamine were introduced into a 1-liter round-bottomed flask.

The contents were cooled to 5° C. and 25 g of ethyl chloroformate were then added in small amounts, while maintaining the temperature between 0° and 5° C.

The mixture was stirred for 1 hour 30 minutes and a solution of 32 g of 1-ethyl-2-aminomethylpyrrolidine in 100 ml of chloroform was then added dropwise, between 5° and 10° C.

The temperature was then allowed to rise and the mixture was then stirred for 1 hour at ambient temperature. The chloroform was distilled off under slight vacuum and the residue was taken up with water and with sufficient acetic acid to bring the pH to 4.

The solution was filtered with charcoal and then made alkaline with 20% ammonia until a color change of phenolphthalein was observed. The oil formed was decanted and extracted with methylene chloride. The solution containing methylene chloride was dried over potassium carbonate and the methylene chloride was distilled off, the distillation towards the end being carried out under vacuum, until a constant weight was obtained. The residue was taken up with water and the solid obtained was drained, washed with water and dried at 40° C.

The 73 g of base obtained were recrystallized in 146 ml of isopropanol and then in 142 ml of absolute ethanol.

Weight obtained: 55 g (m.p.=111°–112° C.; yield=59%).

Example 13
N-(1-Cyclohexenylmethyl-2-pyrrolidinylmethyl)-6-chlorochroman-8-carboxamide fumarate Step I - Preparation of 6-Chlorochroman-8-carbonyl chloride-Intermediate (W-1)

246 g of thionyl chloride and 55 g of 6-chlorochroman-8-carboxylic acid were introduced into a 1-liter round-bottomed flask and the flask was heated in a water bath at 40°–50° C., until the contents dissolved. The contents were slightly cooled, a further 55 g of 6-chlorochroman-8-carboxylic acid were added and the flask was heated again until the contents dissolved.

The contents were then heated in a water bath for 1 hour and the excess thionyl chloride was distilled off under vacuum.

109 g of the chloride of the acid were obtained (yield —91%).

Step II - Preparation of N-(1-Cyclohexenylmethyl-2-pyrrolidinylmethyl)-6-chlorochroman-8-carboxamide (Compound of this Invention)

101 g of 1-cyclohexenylmethyl-2-aminomethylpyrrolidine and 200 ml of methyl ethyl ketone were introduced into a 2-liter round-bottomed flask. The contents were cooled to 5° C. and a solution of 109 g of 6-chlorochroman-8-carbonyl chloride in 500 ml of methyl ethyl ketone was added dropwise, while maintaining the temperature between 0° and 5° C.

The mixture was then allowed to stand for 1 hour at 5° C. and overnight at the ambient temperature.

The product obtained was drained, washed with methyl ethyl ketone and dried at 40° C.

The 195 g of product obtained were redissolved in the heated state in 2 liters of water. The solution was filtered with charcoal and then made alkaline with 20% ammonia until a color change of phenolphthalein was observed. The oil formed was extracted with ether and the ether phase was then dried over potassium carbonate and the ether distilled off, the distillation towards the end being carried out under vacuum, until a constant weight was obtained.

Weight obtained: 177 g (yield −97%).

Step III - Preparation of Title compound: N-(1-Cyclohexenyl-methyl-2-pyrrolidinyl-methyl)-6-chlorochroman-8-carboxamide fumarate 197 g of N-(1-Cyclohexenylmethyl-2-pyrrolidinylmethyl)-6-chlorochroman-8-carboxamide were dissolved in 450 ml of absolute ethanol and 59 g of fumaric acid. The crystals formed on cooling were drained, washed with ethanol and dried at 40° C.

218 g of fumarate were obtained, which were recrystallized in 650 ml of 95% ethanol.

The crystals formed were drained, washed and dried at 40° C.

Weight obtained=196 g (m.p.=166°-167° C.; yield=77%).

Example 14: N-(1-Cyclohexenylmethyl-2-pyrrolidinylmethyl)-5-chloro-2,3-dihydrobenzofuran-7-carboxamide.

Step I - Preparation of 5-Chloro-2 3-dihydrobenzofuran-7-carboxylic acid-Intermediate (X)

34 g of 2,3-dihydrobenzofuran-7-carboxylic acid and 204 ml of acetic acid were introduced into a 1-liter round-bottomed flask and a stream of chlorine was passed through the suspension obtained, while cooling in an ice-salt bath. At the end of 2 to 3 hours, the suspension became fluid. 40 g of chlorine were absorbed. The excess chlorine was then removed by suction under vacuum, by placing a trap containing sodium hydroxide in between. The main part of acetic acid was removed under vacuum and the residue was then taken up with iced water.

The acid obtained was drained, washed with water and dried at 50° C. in a fan-assisted oven.

28.5 g of product were obtained, which were taken up with 30 ml of ether.

The product was drained, washed and dried in air and then at 40° C.

Weight obtained: 20 g (m.p.=226° C.; yield=48%).

Step II - Preparation of Title compound: N-(1-Cyclohexenylmethyl-2-pyrrolidinylmethyl)-5-chloro-2,3-dihydrobenzofuran-7-carboxamide 32 g of 5-chloro-2,3-dihydrobenzofuran-7-carboxylic acid, 130 ml of chloroform and 16 g of triethylamine were introduced into a 1-liter round-bottomed flask. The contents were cooled to 0°-5° C. and 17.5 g of ethyl chloroformate were then added dropwise and the mixture was stirred for 1 hour and 30 minutes. A solution of 34 g of 1-cyclohexenylmethyl-2-aminomethylpyrrolidine in 68 ml of chloroform was then poured in dropwise, between 5° and 10° C., and the mixture was then stirred for 1 hour at 5° C. and for 1 hour at ambient temperature.

The chloroform was distilled off under slight vacuum and the residue was taken up with water and with sufficient acetic acid to adjust the pH to 4. The solution obtained was filtered with charcoal and made alkaline with 30% sodium hydroxide until a color change of phenolphthalein was observed. The precipitate formed was drained, washed with water and dried in a fan-assisted oven at 40° C. 60 g of base were obtained, which were recrystallized in 150 ml of 90% ethanol.

Weight obtained: 39 g (m.p.=104° C.; yield=65%).

Example 15: Neutral ethanedisulphonate of N-(1-cyclohexenylmethyl-2-pyrrolidinylmethyl)-5-chloro-2-methyl-2,3-dihydrobenzofuran-7-carboxamide.

Step I - Preparation of N-(1-Cyclohexenylmethyl-2-pyrrolidinylmethyl)-5-chloro-2-methyl-2,3-dihydrobenzofuran-7-carboxamide (A Compound of this Invention)

51 g of 5-chloro-2-methyl-2,3-dihydrobenzofuran-7-carboxylic acid, 240 ml of chloroform and 24.5 g of triethylamine were introduced into a 1-liter round-bottomed flask. The contents were cooled to 0° C. and 26 g of ethyl chloroformate were then added dropwise, while maintaining the temperature between 0° and 5° C.

The mixture was stirred for 2 hours and 46.5 g of 1-cyclohexenylmethyl-2-aminomethylpyrrolidine were poured in dropwise, between 5° and 10° C. The contents were stirred for 30 minutes, allowing the temperature to rise. The solution was then taken up with water and the pH adjusted to 4 by adding acetic acid. The chloroform was distilled off under vacuum and the solution obtained was then filtered with charcoal and made alkaline with 20% ammonia until a color change of phenolphthalein was observed.

The oil formed was extracted with ether and the solution containing ether was then dried over sodium sulphate and the ether was distilled off, the distillation towards the end being carried out under vacuum, until a constant weight was obtained.

The 83 g of base obtained were dissolved in 332 ml of absolute ethanol. 24.8 g of fumaric acid were added and the mixture heated until the contents dissolved. The crystals formed on cooling were drained, washed with absolute ethanol and dried at 50° C.

The 85 g of fumarate obtained were recrystallized in 500 ml of water. The precipitate formed on cooling was drained, washed with water and dried, and then redissolved in 2 liters of water.

The solution obtained was made alkaline with 20% ammonia until a color change of phenolphthalein was observed.

The oil formed was extracted with ether and the solution containing ether was then dried over sodium sulphate and the ether was distilled off, the distillation towards the end being carried out under vacuum, until a constant weight was obtained.

56 g of an oily product (yield=60%) were obtained.

Step II - Preparation of Title compound: neutral ethanedisulphonate of N-(1-cyclohexenylmethyl-2-pyrrolidinylmethyl)-5-chloro-2-methyl-2,3-dihydrobenzofuran-7-carboxamide 56 g of the base were dissolved in 250 ml of absolute ethanol and 33 g of ethanedisulphonic acid containing 18% water were then added. The mixture was warmed until the contents dissolved. After cooling, the crystals formed were drained, washed with ethanol and dried at 50° C.

The 57 g of product obtained were redissolved in the cold state in 570 ml of water and the solution was then concentrated in a water bath.

The crystals formed on cooling were dried in an oven. After grinding, the product was left exposed to air until its weight became constant.

The product contains 2 moles of water.

Weight obtained: 53 g of hydrated product (m.p.=85°–90° C.; yield=71%).

Example 16: N-(1-Cyclopropylmethyl-2-pyrrolidinylmethyl)-5-amino-6-methylsulphamoylchroman-8-carboxamide hydrochloride.

Step I - Preparation of 5-Bromo-6-chlorosulphonylchroman-8-carboxylic acid-Intermediate (Y)

The acid was prepared according to the procedure in Example 8.

Step II - Preparation of 5-Bromo-6-methylsulphamoylchroman-8- carboxylic acid-Intermediate (Z)

70 g of methylamine in a 40% aqueous solution and 70 ml of water were introduced into a 1-liter round-bottomed flask. The contents were cooled to 0° C. and 160 g of 5-bromo-6-chlorosulphonylchroman-8-carboxylic acid were added in 16 g portions, the introduction of each portion of acid being followed by the addition of 18 ml of a solution containing 90 ml of 30% sodium hydroxide in 90 ml of water. The temperature was maintained between 0° and 5° C. during the entire period of introduction and for a further period of one hour. The temperature was then allowed to rise. The solution obtained was taken up with 1 liter of water, filtered with charcoal and acidified with concentrated hydrochloric acid until a color change of Congo red was observed.

The precipitate formed was drained, washed with water and dried at 40° C. in a fan-assisted oven.

Weight obtained: 142 g (m.p.=234° C.; yield=90%).

Step III - Preparation of 5-Amino-6-methylsulphamoylchroman-8-carboxylic acid-Intermediate (A-1)

75 g of 5-bromo-6-methylsulphamoylchroran-8-carboxylic acid, 284 ml of 34% ammonia, 3 g of copper and 3 g of cuprous chloride were introduced into a 1-liter autoclave.

The contents were heated to 120° C. to 15 hours.

A second trial was carried out under the same conditions and the two solutions, which were diluted with 400 ml of water, were combined.

The solution was filtered with charcoal and acidified with concentrated hydrochloric acid until a color change of Congo red was observed.

The precipitate formed was drained, washed with water and dried to 60° C.

103 g of acid were obtained, which were redissolved in 500 ml of water and 40 ml of 30% sodium hydroxide. The solution obtained was filtered with charcoal and acidified with concentrated hydrochloric acid until a color change of Congo red was observed.

The precipitate formed was drained, washed with water and dried in a fan-assisted oven.

97 g of product (m.p.=250° C.) were obtained, which was recrystallized in 270 ml of dimethylformamide containing 35% of water.

Weight obtained: 67 g (yield=55%).

Step IV - Preparation of N-(1-Cyclopropylmethyl-2-pyrrolidinylmethyl)-5-amino-6-methylsulphamoylchroman-8-carboxamide (A Compound of the Invention)

71 g of 5-amino-6-methylsulphamoylchroman-8-carboxylic acid, 152 ml of dimethylformamide and 25 g of triethylamine were introduced into a 1-liter round-bottomed flask. The contents were cooled to 0° C. and 27 g of ethyl chloroformate were then added dropwise, while maintaining the temperature between 0° and 5° C. The mixture was then maintained at the same temperature for 15 minutes and 28.5 g of 1-cyclopropylmethyl-2-aminomethylpyrrolidine were then poured in dropwise. The temperature was then allowed to rise and the mixture was stirred for 2 hours.

The solution was taken up with water and the pH adjusted to 4 by adding acetic acid. The solution obtained was filtered with charcoal and then made alkaline with 20% ammonia until a color change of phenolphthalein was observed. The oil formed was extracted with methylene chloride and the solution containing methylene chloride was then dried over potassium carbonate. The methylene chloride was then distilled off, the distillation towards the end being carried out under vacuum, until a constant weight was obtained.

Weight obtained: 74 g (yield=70%).

Step V - Preparation of Title compound: N-(1-Cyclopropylmethyl-2-pyrrolidinylmethyl)-5-amino-6-methylsulphamoylchroman-8-carboxamide hydrochloride 105 g of the base were dissolved at 40° C. in 210 ml of methanol and a solution of 9 g of hydrogen chloride gas in 20 ml of methanol was then added. The mixture was allowed to stand overnight and the crystals formed were then drained at 5° C., washed with methanol and dried at 50° C. in a fan-assisted oven. 42 g of hydrochloride were obtained.

The solutions containing methanol were concentrated to dryness under vacuum and the residue was then redissolved in 160 ml of isopropanol. After standing overnight, the crystals formed were drained at 5° C., washed with isopropanol and dried at 50° C. 15 g of product were obtained, which were recrystallized in 75 ml of methanol. 4 g of hydrochloride were collected.

The alcoholic solutions were concentrated to dryness and the residue was then taken up with 95% ethanol and allowed to crystallize overnight. 6 g of hydrochloride were collected.

52 g of hydrochloride were therefore obtained in total, which were redissolved in the heated state in 104 ml of 85% ethanol. The solution was allowed to stand overnight at 0°–5° C. and the crystals formed were then drained, washed with 85% ethanol and with absolute ethanol and dried at 60° C.

36 g of hydrochloride were obtained.

After concentrating the alcoholic solutions to dryness and taking up with absolute ethanol, 7 g of hydrochloride were collected.

Total weight obtained: 43 g (m.p. = 248°–249° C.; yield = 38%).

Example 17:
N-(1-Ethyl-2-pyrrolidinylmethyl)-5-ethylsulphonyl-4-methoxy-2-methyl-2,3-dihydrobenzofuran-7-carboxamide hydrochloride

Step I - Preparation of 5-chlorosulphonyl-4-methoxy-2-methyl-2,3-dihydrobenzofuran-7-carboxylic acid-Intermediate (B-1)

218 g of chlorosulphonic acid were introduced into a 500 ml round-bottomed flask and 65 g of finely ground 4-methoxy-2-methyl-2,3-dihydrobenzofuran-7-carboxylic acid were added in small amounts. The temperature rose to 38° C. The contents were then heated to 50° C. After cooling, the solution obtained was poured, in small amounts, onto ice, with stirring.

The precipitate formed was drained, washed with water and air-dried.

Weight obtained: 76 g (yield = 80%).

Step II - Preparation of 5-Ethylsulphonyl-4-methoxy-2-methyl-2,3-dihydrobenzofuran-7-carboxylic acid-Intermediate (C-1)

220 ml of water, 47 g of sodium sulphite and 62.5 g of sodium bicarbonate were introduced into a 2-liter round-bottomed flask and the contents were then heated to 70° C. 76 g of 5-chlorosulphonyl-4-methoxy-2-methyl-2,3-dihydrobenzofuran-7-carboxylic acid were then added in small amounts. Heating was maintained at 70°–80° C. for 1 hour 30 minutes, until the evolution of carbon dioxide was complete. The contents were then cooled to 20° C. and 256 ml of ethanol, 49.5 ml of 30% sodium hydroxide and 116 g of ethyl iodide were then added. The contents were heated under reflux for 30 hours, the losses of ethyl iodide being replenished and the pH being readjusted by adding sodium hydroxide as soon as the medium was no longer alkaline.

A part of the alcohol was then distilled off, the residue was taken up with water, the solution obtained was filtered and the medium acidified by adding concentrated hydrochloric acid until a color change of Congo red was observed.

The precipitate formed was drained, washed with water and dried at 50° C.

Weight obtained: 52 g (m.p. = 176° C.; yield = 70%).

Step III - Preparation of N-(1-Ethyl-2-pyrrolidinylmethyl)-5-ethylsulphonyl-4-methoxy-2-methyl-2,3-dihydrobenzofuran-7-carboxamide (A Compound of this Invention)

51.5 g of 5-ethylsulphonyl-4-methoxy-2-methyl-2,3-dihydrobenzofuran-7-carboxylic acid, 250 ml of chloroform and 17 g of triethylamine were introduced into a 1-liter round-bottomed flask. The contents were stirred for 30 minutes and then cooled to 5° C. 18.5 g of ethyl chloroformate were then added dropwise, while maintaining the temperature between 0° and 5° C. The mixture was stirred at this temperature for 30 minutes and 22 g of 1-ethyl-2-aminomethylpyrrolidine were then poured in dropwise, between 5° and 10° C. The stirring was then continued at 10° C. for 30 minutes and the temperature was allowed to rise.

The solution was taken up with water and the pH adjusted to 4 by adding acetic acid. The chloroform was distilled off, the remaining aqueous solution was filtered with charcoal and made alkaline by adding 30% sodium hydroxide until a color change of phenolphthalein was observed. The oil formed was decanted and extracted with methylene chloride and the solution containing methylene chloride was dried over potassium carbonate. The methylene chloride was then distilled off, the distillation towards the end being carried out under vacuum, until a constant weight was obtained.

Weight obtained: 63 g (yield = 90%/ m.w. = 424).

Step IV - Preparation of Title compound: N-(1-Ethyl-2-pyrrolidinylmethyl)-5-ethylsulphonyl-4-methoxy-2-methyl-2,3-dihydrobenzofuran-7-carboxamide hydrochloride.

62.5 g of base were dissolved in the heated state in 130 ml of ethanol and 12.5 ml of concentrated hydrochloric acid (11.8N). After cooling, the crystals formed were drained, washed with 95% ethanol and dried at 40° C.

The 48 g of product obtained were recrystallized in 96 ml of 95% ethanol. The boiling solution was filtered with charcoal. After cooling, the crystals formed were drained, washed with 95% ethanol and dried at 40° C.

Weight obtained: 41 g of hydrochloride containing 1 mole of water (m.p. = 138°–140° C.; yield = 60%).

Example 18:
N-(1-Ethyl-2-pyrrolidinylmethyl)-5-methyl-6-ethylsulphonylchroman-8-carboxamide.

Step I - Preparation of Methyl 2-allyloxy-4-methylbenzoate-Intermediate (D-1)

265 g of potassium carbonate, 637 ml of acetonitrile, 300 g of benzyl tributylammonium and 279 g of allyl bromide were introduced into a 4-liter round-bottomed flask and 391.5 g of methyl 2-hydroxy-4-methylbenxzoate were then added slowly. The temperature rose up to 36° C. The contents were then heated under reflux, with vigorous stirring, for 4 hours and then cooled and the reaction mixture poured into 7 liters of water. The oily layer formed was decanted and extracted with ether and the solution containing ether was then dried over sodium sulphate. The ether was then distilled off, the distillation towards the end being carried out under vacuum, until a constant weight was obtained.

Weight obtained: 388.5 g (yield = 98%).

Step II - Preparation of Methyl 2-hydroxy-3-allyl-4-methylbenzoate-Intermediate (E 1)

194 g of methyl 2-allyloxy-4-methylbenzoate were introduced into a 1 liter round bottomed flask. The contents were heated gently to boiling and the heating then discontinued. The reaction continued unaided, with the evolution of heat. The same operations were repeated with a second portion of 194 g, and the combined products obtained were distilled at the end of the two trials. The fraction distilling at 160°–163° C. at 23 mm Hg was collected.

Weight obtained: 355 g (yield=92%).

Step III - Preparation of Methyl 2-acetoxy-3-allyl-4-methylbenzoate-Intermediate (F-1)

351 g of acetic anhydride followed by 2.5 ml of sulphuric acid (d=1.84) in small amounts, and finally, 355 g of methyl 2-hydroxy-3-allyl-4-methylbenzoate were introduced into a 2-liter round-bottomed flask. The temperature rose up to 35° C. The contents were heated under reflux for 3 hours and the solution obtained was then poured into 2 liters of iced water. The oily layer formed was decanted and extracted with ether and the solution containing ether was dried over sodium sulphate.

After removing the ether, the product remaining was distilled under vacuum.

Weight obtained: 350 g (yield=82%).

Step IV - Preparation of Methyl 2-acetoxy-3-(gamma-bromopropyl)-4-methylbenzoate-Intermediate (G-1)

350 g of methyl 2-acetoxy-3-allyl-4-methylbenzoate, 1060 ml of carbon tetrachloride and 3.7 g of benzoyl peroxide were introduced into a 3-liter round-bottomed flask. The solution obtained was cooled to −5° C. and a stream of hydrogen bromide gas was passed through the solution until the weight of the reaction mixture increased by 132 g, the temperature being maintained between −5° C. and 0° C. throughout the period of absorption.

The contents were stirred for 30 minutes and allowed to stand overnight. The solution was then taken up with 2 liters of water and the organic phase was decanted and the aqueous phase extracted with carbon tetrachloride. The organic phases were combined, washed with a 4% sodium bicarbonate solution and then dried over sodium sulphate.

The carbon tetrachloride was then distilled off, the distillation towards the end being carried out under vacuum, until a constant weight was obtained.

Weight obtained: 438 g (yield=94%).

Step V - Preparation of 5-Methylchroman-8-carboxylic acid-Intermediate (H-1)

438 g of methyl 2-acetoxy-3-(gamma-bromopropyl)-4-methylbenzoate and 2660 ml of 10% sodium hydroxide were introduced into a 6 liter round-bottomed flask and the contents were heated under reflux for 2 hours.

The solution obtained was taken up with water, filtered with charcoal and acidified with concentrated hydrochloric acid until a color change of Congo red was observed. The precipitate obtained was drained, washed with water and dried at 40° C. 253 g of product were obtained, which were redissolved in the heated state in 506 ml of isopropyl alcohol.

After cooling, the crystals formed were drained, washed with 100 ml of isopropyl alcohol and then dried at 40° C.

Weight obtained: 158 g (m.p.=140° C.; yield=62%).

Step VI - Preparation of 6-Chlorosulphonyl-5-methylchroman-8-carboxylic acid-Intermediate (I-1)

725 ml of chlorosulphonic acid were introduced into a 2 liter round-bottomed flask. The contents were cooled to 5° C. and 139 g of 5-methylchroman-8-carboxylic were then added in small amounts, while maintaining the temperature between 55° and 10° C.

The temperature was then allowed to rise and the reaction mixture was allowed to stand overnight.

The solution obtained was poured onto 5 kg of ice with external cooling in a solid carbon dioxide-alcohol bath. The precipitate formed was drained, washed with water and air-dried.

Weight obtained: 211 g.

Step VII - Preparation of 6-Ethylsulphonyl-5-methylchroman-8-carboxylic acid-Intermediate (J-1)

855 ml of water, 137 g of sodium sulphite and 183 g of sodium bicarbonate were introduced into a 6-liter round-bottomed flask. The contents were heated to 70° C. with stirring and 211 g of 5-methyl-6-chlorosulphonylchroman-8-carboxylic acid were then added in small amounts, while maintaining the temperature between 70°-80° C. The contents were then heated for 2 hours at 70°-80° C. until the evolution of carbon dioxide was complete.

The contents were then cooled to 20° C. and 511 ml of ethanol, 145 ml of 30% sodium hydroxide and 340 g of ethyl iodide were added and the contents were then heated under reflux, the losses of ethyl iodide being replenished and sodium hydroxide being added as soon as the medium was no longer alkaline. The reflux temperature rose from 56° C. to 84° C. after 30 hours.

A part of the alcohol was then distilled off and the residue taken up with water. The solution obtained was filtered and acidified with concentrated hydrochloric acid until a colour change of Congo red was observed. The precipitate formed was drained, washed with water and dried at 50° C. 161 g of product were obtained, which were recrystallized in 322 ml of 2-ethoxyethanol.

Weight obtained: 115 g (m.p.=190° C.; yield=56%).

Step VIII - Preparation of Title compound: N-(1-Ethyl-2-pyrrolidinylmethyl)-5-methyl-6-ethylsulphonylchroman-8-carboxamide 28.5 g of 5-methyl-6-ethylsulphonylchroman-8-carboxylic acid, 100 ml of chloroform and 10 g of triethylamine were introduced into a 250-ml round-bottomed flask. The contents were cooled to 0° C. and 11 g of ethyl chloroformate were added dropwise, between 0° and 5° C. The contents were stirred for 2 hours at the same temperature and 13 g of 1-ethyl-2-aminomethylpyrrolidine were then poured in dropwise, between 5° and 10° C. The temperature was then allowed to rise and the contents were stirred for 1 hour.

The solution obtained was taken up with 250 ml of water and sufficient acetic acid to bring the pH to 4. The chloroform was removed by carrying over with water and the aqueous solution remaining was filtered with charcoal and made alkaline with 20% ammonia until a color change of phenolphthalein was observed. The precipitate formed was drained, washed with water and dried at 40° C.

36 g of base were obtained, which were recrystallized in 68 ml of absolute ethanol. The 31 g of product obtained were recrystallized in 62 ml of absolute ethanol.

Weight obtained: 28 g (m.p.=149° C.; yield=71%).

Example 19:
N-(1-Cyclopropylmethyl-2-pyrrolidinylmethyl)-5-methyl-6-ethylsulphonylchroman-8-carboxamide 66 g of 5-methyl-6-ethylsulphonylchroman-8-carboxylic acid, 232 ml of chloroform and 23.5 g of triethylamine were introduced into a 1-liter round-bottomed flask. The temperature rose up to 40° C. The contents were then cooled to 0° C. and 25 g of ethyl chloroformate were then added dropwise, while maintaining the temperature between 0° and 5° C. The contents were then stirred for 2 hours between 0° and 5° C. and 36 g of 1-cyclopropylmethyl-2-aminomethylpyrrolidine were then poured in dropwise, between 5° and 10° C. The temperature was then allowed to rise and the mixture was stirred for 1 hour.

The solution obtained was taken up with 2 liters of water and the pH was adjusted to 4 by adding acetic acid. The chloroform was then carried over with water and the aqueous solution remaining was filtered with charcoal and made alkaline with 20% ammonia until a color change of phenolphthalein was observed.

The crystals formed were drained, washed with water and air-dried. 87 g of base were obtained (yield=89%). 81 g of base were dissolved in 255 ml of absolute ethanol and a solution of 7 g of hydrogen chloride gas in 30 ml of ethanol were then added until a color change of methyl red was observed. The crystals formed were drained, washed with 60 ml of ethanol and dried at 50° C. 82 g of the hydrochloride were obtained, which were recrystallized in 164 ml of 95% ethanol. The crystals formed on cooling were drained, washed with 95% ethanol and then with ether, and dried in air and then at 50° C. 78 g of hydrochloride (m.p.=212° C.) were obtained.

The 78 g of hydrochloride were dissolved in a cooled state in 1 liter of water. The solution obtained was filtered and then made alkaline with 20% ammonia until a color change of phenolphthalein was observed. The base obtained was drained, washed with water and dried at 40° C.

Weight obtained: 68 g (m.p.=100° C., yield=75%).

Example 20:
N-(Diethylaminoethyl)-4-amino-5-chloro-2-methyl-2,3-dihydrobenzofuran-7-carboxamide.

Step I - Preparation of Methyl 2-allyloxy4-acetaminobenzoate-Intermediate (K-1)

138 g of potassium carbonate, 16.5 g of benzyltributylammonium chloride, 650 ml of acetonitrile and 133 g of allyl bromide were introduced into a 2-liter round-bottomed flask and 209 g of ground methyl 2-hydroxy-4-acetaminobenzoate were then added in small amounts. The contents were heated under reflux for 11 hours, a part of the acetonitrile was then distilled off and the residue was taken up with water. The precipitate formed was drained, washed with water and dried in an oven at 50° C.

Weight obtained: 240.5 g (m.p.=121° C.; yield=96.5%).

Step II - Preparation of Methyl 2-hydroxy3-allyl-4-acetaminobenzoate-Intermediate (L-1)

84 g of methyl 2-allyloxy-4-acetaminobenzoate and 84 g of N-methylpyrrolidone were introduced into a 500 ml round-bottomed flask. The contents were heated quickly to reflux which was then maintained for 30 minutes, and the solution was then cooled slightly and poured into water. Crystallization was immediate. The same operations were repeated with the same quantities of methyl 2-allyloxy-4-acetaminobenzoate and N-methylpyrrolidone and the products from the two trials were combined and cooled, drained, washed with water and dried at 50° C.

158 g of product were obtained, which were redissolved on boiling in 450 ml of 2-methoxyethanol.

The product obtained on cooling was drained, washed with 2-methoxyethanol and dried at 50° C.

Weight obtained: 118 g (yield=70%).

Step III - Preparation of Methyl 2-hydroxy-3-(gamma-bromopropyl)-4-acetaminobenzoate-Intermediate (M-1)

2277 g of 66% hydrobromic acid and 308 g of methyl 2-hydroxy-3-allyl-4-acetaminobenzoate were introduced into a 3-liter round-bottomed flask equipped with a leakproof stirrer, a thermometer and a safety tube containing mercury so that a pressure of approximately 2 cm of mercury is created in the apparatus. The mixture was stirred for 4 hours and then allowed to stand overnight. 5 liters of water were then added. The precipitate formed was drained, washed with water and dried at 50° C.

Weight obtained=302 g (m.p.=159° C.; yield=74%.

Step IV - Preparation of Methyl 2-hydroxy-3-(gamma-bromopropyl)-4-acetamino-5-chloro-benzoate-Intermediate (N-1)

250 g of methyl 2-hydroxy-3-(gamma-bromopropyl)-4-acetaminobenzoate and 1250 ml of acetic acid were introduced into a 3-liter round-bottomed flask and a stream of chlorine was then passed through slowly, while cooling, so as to maintain the temperature between 20° and 25° C.

The reaction was complete in 3 hours, after 74 g of chlorine were absorbed.

The reaction mixture was then taken up with 9 liters of water and the product obtained was drained, washed with water and dried at 50° C.

Weight obtained: 265 g (m.p.=175° C.; yield=96%).

Step V - Preparation of 4-Amino-5-chloro-2-methyl-2,3-dihydrobenzofuran-7-carboxylic acid-Intermediate (O-1)

1450 ml of 10% sodium hydroxide and 265 g of methyl 2-hydroxy-3-(gamma-bromopropyl)-4-acetamino-5-chlorobenzoate were introduced into a 4-liter round-bottomed flask. The flask was heated until the contents were completely dissolved and then heated under reflux for 3 hours.

The solution obtained was taken up with 1450 ml of water and then filtered with charcoal and acidified with concentrated hydrochloric acid until a color change of Congo red was observed. The precipitate formed was drained, washed with water and dried at 50° C.

139 g of product were obtained, which were recrystallized in 278 ml of isopropanol.

The 97 g of product obtained were dissolved in 1 liter of water and 160 ml of 30% sodium hydroxide. The solution obtained was filtered with charcoal and then allowed to stand for a few hours, after adding 5 g of sodium bisulphite. The solution was then acidified with 140 ml of concentrated hydrochloric acid. The precipitate formed was drained, washed with water and dried at 50° C.

Weight obtained: 90 g (m.p.=178° C.; yield=54.5%).

Step VI - Preparation of Title compound: N-(Diethylaminoethyl)-4-amino-5-chloro-2-methyl-2,3-dihydrobenzofuran-7-carboxamide 56 g of 4-amino-5-chloro-2-methyl-2,3-dihydrobenzofuran-7-carboxylic acid, 200 ml of chloroform and 25 g of triethylamine were introduced into a 1-liter round-bottomed flask.

The mixture was cooled to 5° C. and 27 g of ethyl chloroformate were then poured in dropwise, while maintaining the temperature between 5° and 10° C. The contents were stirred for 30 minutes at 10° C. and 30 g of diethylaminoethylamine were then poured in dropwise, between 10° and 15° C. The stirring was then continued at 10° C. and the temperature was then allowed to rise. The chloroform was then distilled off under slight vacuum and the residue was then taken up with acidified water. The solution obtained was filtered with charcoal and made alkaline by adding 20% ammonia until a color change of phenolphthalein was observed. The product obtained was drained, washed with water and air-dried.

The 68 g of base obtained were dissolved in the heated state in 180 ml of isopropanol and 24 g of fumaric acid.

The precipitate of fumarate, which was formed by cooling, was drained, washed with isopropanol and dried at 40° C. 76 g of product were obtained, which were recrystallized in 152 ml of absolute ethanol.

The 61 g of fumarate obtained were redissolved in 600 ml of water. 2 g of sodium metabisulphite were added and the solution was then filtered with charcoal and 20% ammonia was added until a color change of phenolphthalein was observed. The crystals formed were drained, washed with water and dried.

The 43 g of base obtained were treated with 15.5 g of fumaric acid in 120 ml of absolute ethanol.

The 49.5 g of fumarate formed were dissolved in 520 ml of water. The solution was filtered and then made alkaline by adding 20% ammonia until a color change of phenolphthalein was observed. The precipitate formed was drained, washed with water and dried at 40° C.

34 g of base (m.p.=88°–89° C.; yield=42%) were obtained.

Example 21:
N-Methyl-N-(diethylaminoethyl)-4-amino-5-chloro-2-methyl-2,3-dihydrobenzofuran-7-carboxamide citrate.

Step I - Preparation of N-Methyl-N-(diethylaminoethyl)-4-amino-5-chloro-2-methyl-2,3-dihydrobenzofuran-7-carboxamide (Compound of this Invention)

86.5 g of 4-amino-5-chloro-2-methyl-2,3-dihydrobenzofuran-7-carboxylic acid, 350 ml of chloroform and 38.5 g of triethylamine were introduced into a 1-liter round-bottomed flask. The mixture was cooled to 0° C. and 41.5 g of ethyl chloroformate were then poured in dropwise, while cooling so as to maintain the temperature below 5° C. The mixture was stirred for 30 minutes between 0° and 5° C. and 52 g of N-methyl-N'-diethylaminoethyl-amine were then poured in dropwise, between 5° and 10° C. The contents were then stirred for 1 hour at 10° C. and the temperature was allowed to rise. The chloroform was then distilled off under slight vacuum and the residue was taken up with water and sufficient acetic acid to adjust the ph to 4. The solution obtained was filtered with charcoal and then made alkaline by adding 20% ammonia until a color change of phenolphthalein was observed. The oil formed was decanted and extracted with methylene chloride. The solution containing methylene chloride was dried over potassium carbonate and the methylene chloride was distilled off, the distillation towards the end being carried out under vacuum, until a constant weight was obtained.

Weight obtained: 111 g of product containing 77% of benzamide and 23% of N-methyl-N-carbethoxy-N'-diethylaminoethylamine.

93 g of the product obtained were dissolved in the heated state in 300 ml of acetonitrile and 69 g of ethanedisulphonic acid dihydrate. A small quantity of acetonitrile was then distilled off so as to carry over as much water as possible.

The solid product formed on cooling was drained, washed with acetonitrile and dried at 40° C. 116 g of ethanedisulphonate were obtained, which were dissolved in water. The solution was filtered with charcoal and made alkaline by adding 20% ammonia until a color change of phenolphthalein was observed. The oil formed was decanted and extracted with ether and the solution containing ether was then dried over potassium carbonate and the ether was distilled off, the distillation towards the end being carried out under vacuum, until a constant weight was obtained. 62 g of base were obtained, which were dissolved in the heated state in 210 ml of acetonitrile and 42 g of ethanedisulphonic acid dihydrate. A part of the acetonitrile was distilled off under slight vacuum. The crystals formed on cooling were drained, washed with acetonitrile and dried at 40° C. 86 g of ethanedisulphonate were obtained, which were dissolved in 800 ml of water. The solution obtained was made alkaline by adding 20% ammonia until a color change of phenolphthalein was observed. The oil formed was extracted with ether and the solution containing ether was dried over potassium carbonate and the ether distilled off, the distillation towards the end being carried out under vacuum, until a constant weight was obtained.

Weight obtained: 51.5 g (yield=49%).

Step II - Preparation of Title compound: N-Methyl-N-(diethylaminoethyl)-4-amino-5-chloro-2-methyl-2,3-dihydrobenzofuran-7-carboxamide citrate.

51.5 g of N-methyl-N-(diethylaminoethyl)-4-amino-5-chloro-2-methyl-2,3-dihydrobenzofuran-7-carboxamide were dissolved in the heated state in 160 ml of ethanol and 29 g of citric acid and the solution obtained was then cooled. The crystals formed were drained, washed with absolute ethanol and dried at 40° C.

The 75 g of citrate obtained were redissolved in the heated state in 150 ml of absolute ethanol. The precipitate formed by cooling was suspended in the cold state in 150 ml of absolute ethanol and then allowed to stand overnight. The precipitate was then drained, washed with ethanol and dried at 40° C.

Weight obtained: 67 g (m.p.=119°–120° C.; yield=83%).

The compounds of the invention formed the subject of a toxicological and pharmacological study.

Acute toxicity was studied in mice, the compounds being administered intravenously, subcutaneously, intraperitoneally and orally.

The doses causing the death of 50% of the animals ($LD_{50}$) were determined by Bliss' method, giving the following results:

| Compound | Lethal doses$_{50}$ expressed in mg/kg | | | |
|---|---|---|---|---|
| | i.v. | s.c. | i.p. | orally |
| Ex 1 | 30.5–35.2 | 316–318 | 134–152 | 259–295 |
| Ex 2 | 42.6–43.7 | 406–408 | 167–172 | 342–354 |
| Ex 3 | 14–16 | 250 | 117–125 | 166–170 |
| Ex 4 | 65.2–67.6 | 375–382 | 188–195 | 502–548 |
| Ex 5 | 68.4–69.9 | 385–412 | 261–261 | 417–430 |
| Ex 6 | 37.9–46.1 | 291–312 | 163–165 | 408–412 |
| Ex 7 | 60.9–63.3 | 415–435 | 239–266 | 479–532 |
| Ex 8 | 58.2–58.7 | 239–251 | 167–179 | 490–518 |
| Ex 9 | 68.8–70.2 | 440–462 | 211–213 | 390–391 |
| Ex 10 | 29.1–29.8 | 263–282 | 111–112 | 156–166 |
| Ex 11 | 28–28.6 | 141–145 | 125–127 | 149–163 |
| Ex 12 | 68.5–71 | 376–390 | 224–228 | 499–518 |
| Ex 13 | 18.6–18 | 0% at 900 mg/kg | 120–120 | 422–473 |
| Ex 14 | 24.8 | 412–434 | 69.6–83.3 | 350–354 |
| Ex 15 | 31.1–34.7 | 1407 | 232–234 | 561–521 |
| Ex 16 | 38.2 | 330–382 | 195 | 794–721 |
| Ex 17 | 80.5–86.6 | 280–282 | 230–242 | 367–374 |
| Ex 18 | 95.9–98.1 | 351–375 | 201–217 | 468–524 |
| Ex 19 | 58.5–61.6 | 389–402 | 172–187 | 420–429 |
| Ex 20 | 41–41.4 | 88.4–93.1 | 80.3–81.6 | 147–150 |
| Ex 21 | 42.5 | 281–278 | 191–182 | 309–334 |

It was believed that the compounds of the invention would exhibit neuroleptic properties.

Accordingly, a study of the action of compounds of the invention on the central nervous system was performed by applying classical tests designed to demonstrate a neuroleptic property. Thus, an inhibitory effect on spontaneous motor function in mice, a catalepsy-inducing power in rats, and antagonism towards certain apomorphine- and amphetamine-induced behavioural effects were investigated, in particular.

Regarding the spontaneous motor function in mice, an inhibitory effect of the inventive compounds was effectively observed and recorded by a photoelectric method, according to a technique similar to that of Winter and Flataker (J. Pharmacol. Exp. Ther. 1951, 101, 156–162) and by measurement of activity using an Animex apparatus.

The compounds were administered intraperitoneally or orally, respectively, 15 or 60 minutes before the recording according to the method adopted.

The values of the 50% inhibitory doses of motor function ID$_{50}$ of the compounds are collected in the following table:

| | Inhibition of spontaneous motor function in mice | | | |
|---|---|---|---|---|
| | Winter and Flataker test | | Animex activity measurement test | |
| Compound | ID$_{50}$ i.p. (mg/kg) | ID$_{50}$ p.o. (mg/kg) | ID$_{50}$ i.p. (mg/kg) | ID$_{50}$ p.o. (mg/kg) |
| Ex 1 | 1.8 | 12.4–13.2 | 2.15–3.4 | 19.2–22.4 |
| Ex 2 | 6.2 | 31.5 | 7.5 | 31.5 |
| Ex 3 | 1.21 | 17.3 | 0.55 | 8.5 |
| Ex 5 | 5.6 | 65 | 4.8 | 48 |
| Ex 6 | 15.4 | 55 | 11.4 | 40 |
| Ex 7 | 9.2 | 33.9 | 12.8 | 35.8 |
| Ex 9 | 3.2 | 31.5 | 3 | 23.4 |
| Ex 11 | 1.3 | 16.6 | 1.22 | 16.6 |
| Ex 13 | 1.96 | 20.9 | 3 | 22.7 |
| Ex 14 | 2.1 | 27 | 1.7 | 25 |
| Ex 15 | 3.5 | 43.4 | 2.2 | 23.2 |
| Ex 20 | 11.8 | 32 | 12.8 | 36 |

The catalepsy-inducing function of the compounds of the invention was studied in rats. Each of the compounds was administered subcutaneously, at increasing doses, to groups of 10 rats (1 group for each dose). Each group was observed for 7 hours and the percentage of animals showing catalepsy was established every hour, the criterion of the cataleptic state being immobility for 30 seconds with the rat's forelimbs spread and placed on cubes of wood 3 cm high.

The dose giving rise to catalepsy in 50% of the animals (ED$_{50}$) was determined graphically, at the peak of effect.

The values obtained are shown in the following Table:

| Catalepsy in rats subcutaneouslyy - in mg/kg | | | |
|---|---|---|---|
| Compound | ED$_{50}$ | Compound | ED$_{50}$ |
| Ex 1 | 6.6 | Ex 11 | 1.66 |
| Ex 2 | 17.6 | Ex 13 | 1.5 |
| Ex 3 | 2.3 | Ex 14 | 2.7 |
| Ex 9 | 20.7 | Ex 15 | 1.35 |

Apomorphine and amphetamine induce stereotyped movements in rats which are antagonized by neuroleptics. Different doses of apomorphine administered by different routes were applied to produce these movements.

1.25 mg/kg intravenously, as in the test recommended by Janssen (Arzn. Forsch. 1960, 10, 1003–1005), the test compound being administered subcutaneously 60 minutes before and the observation of the antagonism being made 20 minutes after the administration of the apomorphine, or 0.50 mg/kg subcutaneously, according to a technique derived from that of Puech (Eur. J. Pharmacol. 1978, 50, 291–300), the compound being administered intraperitoneally 30 minutes before and the effect being observed 20 minutes after the administration of the apomorphine.

In the test using dexamphetamine, carried out according to the technique of Janssen (Arz. Forsch. 1961, 11, 932–938), 10 mg/kg of dexamphetamine were injected intravenously, the test product being injected simultaneously subcutaneously, and the effect being measured 60 minutes after these injections.

These different experimental conditions made it possible to establish the doses which antagonize stereotypy by 50% (ID$_{50}$), judged on the basis of the various components of the movements which were observed.

These ID$_{50}$ values are collected in the following table:

| Antagonism of the apomorphine and amphetamine effects in rats | | | |
|---|---|---|---|
| | Apomorphine stereotypy (1.25 mg/kg IV) | Apomorphine stereotypy (0.5 mg/kg SC) | Janssen amphetamine test |
| Compound | ID$_{50}$ S.C. (mg/kg) | ID$_{50}$ I.P. (mg/kg) | ID$_{50}$ S.C. (mg/kg) |
| Ex 1 | 0.375 | 0.64–0.65 | 0.285 |
| Ex 2 | 0.73 | 2.5–2.7 | 0.77 |
| Ex 3 | 0.084 | | 0.078 |
| Ex 5 | 2.45 | 1.6–1.9 | 0.65 |
| Ex 6 | 13.2 | 9.4–11.1 | 4.2 |
| Ex 7 | 9.5 | 7.1–8.1 | 3.9 |
| Ex 9 | 3.6 | 1.2–1.6 | 1.1 |
| Ex 10 | 5.4 | 7.8–9.3 | 2.7 |
| Ex 11 | 0.134 | 0.18–0.23 | 0.066 |
| Ex 12 | 17 | 5.3–6 | 10.6 |
| Ex 13 | 0.22 | 0.38–0.44 | 0.15 |
| Ex 14 | 0.29 | 0.31–0.41 | 0.12 |
| Ex 15 | 0.41 | 0.58–0.59 | 0.18 |
| Ex 20 | 13.2 | 5.2–5.6 | 8 |

Another test using apomorphine was applied, based on the observation of the climbing behavior which it induces in mice, this behavior being antagonized by neuroleptics, according to Puech (Eur. J. Pharmacol. 1978, 50, 291-300).

The compound was administered intraperitoneally 30 minutes before the apomorphine (1 mg/kg subcutaneously), and the antagonism was assessed 45 to 50 minutes after the administration of the compound.

The doses inhibiting 50% of this behavior ($ID_{50}$), determined under these conditions, are shown in the following table:

| Antagonism of apomorphine-induced climbing behavior in mice | | | |
|---|---|---|---|
| Compound | $ID_{50}$ I.P. (mg/kg) | Compound | $ID_{50}$ I.P. (Mg/kg) |
| Ex 1 | 0.55-0.63 | Ex 11 | 0.105-0.126 |
| Ex 2 | 1.20-1.24 | Ex 12 | 3.1-4.5 |
| Ex 5 | 0.67-0.69 | Ex 13 | 0.32-0.35 |
| Ex 6 | 3.2-3.5 | Ex 14 | 0.27-0.29 |
| Ex 7 | 3.3-4.1 | Ex 15 | 0.28-0.34 |
| Ex 9 | 0.40-0.55 | | |

The results obtained by the tests described above show that the compounds of the invention are capable, sometimes at very low doses, of inhibiting spontaneous motor function in mice, of inducing catalepsy in rats and of antagonizing certain types of behavior (stereotypy, climbing) induced by apomorphine or amphetamine in mice or rats.

Accordingly, the compounds of the invention possess typical pharmacological properties of neuroleptics, some of the compounds being very powerful in this respect.

The clinical trials carried out with the compounds of the invention have confirmed their neuroleptic potential revealed by the pharmacological study.

Pharmaceutical Compositions

The compounds of the invention can be administered in any number of conventional forms such as capsules, tablets, pills, in granulated form or as an injectable solution. Many methods for compounding these preparations are well-known to the art. Substances which are inert relative to the compounds of the invention can be used in these preparations, such as lactose, magnesium, stearate, starch, talc, cellulose, levilite, alkali metal lauryl-sulphates, saccharose and other vehicles commonly employed in pharmaceutical preparations.

The compounds may be administered in doses of about 50-1000 mg per day taken in 1 or more stages.

The examples which follow illustrate several pharmaceutical preparations, which can be made in a conventional manner from the compounds of the invention.

| EXAMPLE 22 - tablets | |
|---|---|
| N-(1-Cyclohexenylmethyl-2-pyrrolidinylmethyl)-5-methylsulphamoyl-2-methyl-2,3-dihydrobenzofuran-7-carboxamide | 100 mg |
| dried starch | 20 mg |
| lactose | 100 mg |
| methylcellulose 1500 cps | 1.5 mg |
| levilite | 10 mg |
| magnesium stearate | 4 mg |
| for 1 tablet. | |

| EXAMPLE 23 - capsules | |
|---|---|
| N-(1-allyl-2-pyrrolidinylmethyl)-6-cyclopropyl-methylsulphonyl chroman-8-carboxamide | 50 mg |
| microcrystalline cellulose | 50 mg |
| methylcellulose 1500 cps | 1 mg |
| magnesium stearate | 5 mg |
| talc | 2 mg |
| for 1 capsule | |

| EXAMPLE 24 - injectable solution | |
|---|---|
| N-(diethylaminoethyl-4-amino-5-chloro-2-methyl-2,3-dihydrobenzofuran-7-carboxamide | 40 mg |
| 1N hydrochloric acid | 0.1 ml |
| sodium chloride | 14 mg |
| for 2 ml. | |

| EXAMPLE 25 - injectable solution | |
|---|---|
| N-(1-cyclohexenylmethyl 2-pyrrolidinylmethyl)-6-methylsulphamoylchroman-8-carboxamide | 100 mg |
| 1N hydrochloric acid | 0.250 ml |
| sodium chloride | 8 mg |
| for 2 ml. | |

To prepare the tablets, the selected compound is mixed with the starch and lactose by the method of successive dilutions; the mixture is granulated with methylcellulose. The levilite, magnesium stearate and talc are added to the granules before proceeding with compression.

It is possible to replace the methylcellulose with any other appropriate granulating agent, such as ethylcellulose, polyvinylpyrrolidone or starch paste. The magnesium stearate may be replaced by stearic acid.

When preparing injectable solutions, it is possible to dissolve the compound of the invention in the following acids: hydrochloric or levulinic acid, gluconic acid, or glucoheptonic acid. The solution is prepared under sterile conditions and made isotonic with an alkali metal chloride such as sodium chloride, then preservatives are added. It is also possible to prepare the same solution without adding any preservatives: the ampoule is then filled under nitrogen and sterilized for ½ hour at 100° C.

What is claimed is:

1. Dihydrobenzofuran- and chroman-carboxamide derivatives of formula (I):

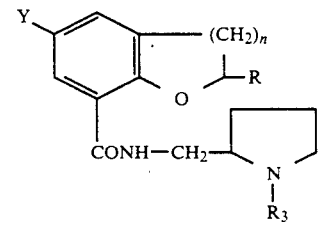

in which R is hydrogen or methyl;
n is equal to 1 or 2;
$R_3$ is cyclopropylmethyl or cyclohexanylmethyl;
Y is chlorine, cyclopropylmethylsulphonyl, methylsulfamoyl or ethylsulphonyl, and their pharmacologically acceptable acid addition salts and their optical isomers.

2. According to claim 1, N-(1-cyclohexyl-methyl-2-pyrrolodinylmethyl)-5-methylsulphamoyl-2-methyl-2,3-dihydrobenzofuran-7-carboxamide.

3. According to claim 1, N-(1-cyclohexenyl-methyl-2-pyrrolidinylmethyl)-6-methylsulphamoylchroman-8-carboxamide.

4. According to claim 1, N-(1-cyclohexenyl-methyl-2-pyrrolidinylmethyl)-5-cyclopropylmethylsulphonyl-2-methyl-2,3-dihydrobenzofuran-7-carboxamide.

5. According to claim 1, N-(1-cyclopropyl-methyl-2-pyrrolidinylmethyl)-6-cyclopropylmethylsulphonylchroman-8-carboxamide.

6. According to claim 1, N-(1-cyclopropyl-methyl-2-pyrrolidinylmethyl)-6-ethylsulphonylchroman-8-carboxamide.

7. According to claim 1, N-(1-cyclopropyl-methyl-2-pyrrolidinylmethyl)-5-ethylsulphonyl-2-methyl-2,3-dihydrobenzofuran-7-carboxamide.

8. According to claim 1, N-(1-cyclohexenyl-methyl-2-pyrrolidinylmethyl)-6-ethylsulphonylchroman-8-carboxamide.

9. According to claim 1, N-(1-cyclohexenyl-methyl-2-pyrrolidinylmethyl)-6-chlorochroman-8-carboxamide.

10. According to claim 1, N-(1-cyclohexenyl-methyl-2-pyrrolidinylmethyl)-5-chloro-2,3-dihydrobenzofuran-7-carboxamide.

11. According to claim 1, N-(1-cyclohexenyl-methyl-2-pyrrolidinylmethyl)-5-chloro-2-methyl-2,3-dihydrobenzofuran-7-carboxamide.

12. A pharmaceutical composition comprising a compound of formula (I) according to any one of claims 1, 2, 4, and 5–11, in amounts sufficient to provide therapeutic neuroleptic activity and a pharmaceutically acceptable excipient.

* * * * *

UNITED STATES PATENT AND TRADEMARK OFFICE
CERTIFICATE OF CORRECTION

PATENT NO. : 5,006,570

DATED : April 9, 1991

INVENTOR(S) : JACQUELINE FRANCESCHINI, ET AL.

It is certified that error appears in the above-identified patent and that said Letters Patent is hereby corrected as shown below:

COLUMN 3

Line 66, "filtered," should read --drained,--.

COLUMN 9

Line 15, "round bottomed" should read --round-bottomed--.
    Line 66, "round bot-" should read --round-bot- --.

COLUMN 11

Line 23, "phenol-phthalein" should read --phenolphthalein--.

COLUMN 12

Line 16, "m.p.=38°C." should read --m.p.=38°C.).--.

COLUMN 13

Line 23, "(yield=72%" should read --(yield=72%;--.
    Line 36, "m.p.=167°C." should read --m.p.=167°C.).--.

COLUMN 14

Line 8, "m.p.=177°C." should read --m.p.=177°C.).--.

COLUMN 15

Line 45, "Invention" should read --Invention)--.
    Line 66, "and" should read --end--.

UNITED STATES PATENT AND TRADEMARK OFFICE
CERTIFICATE OF CORRECTION

PATENT NO. : 5,006,570

DATED : April 9, 1991

INVENTOR(S) : JACQUELINE FRANCESCHINI, ET AL.

It is certified that error appears in the above-identified patent and that said Letters Patent is hereby corrected as shown below:

COLUMN 17

Line 24, "obtained;" should read --obtained:--.
    Line 64, "an" should read --and--.

COLUMN 21

Line 10, "cyclohexenylmethyl" should read
           --Cyclohexenylmethyl--.
    Line 64, "methylsulphamoylchroran" should read
           --methylsulphamoylchroman--.

COLUMN 24

Line 58, "Intermediate (E 1)" should read
           --Intermediate (E-1)--.
    Line 61, "round bottomed" should read --round-bottomed--.

COLUMN 25

Line 67, "boxylic were" should read --boxylic acid were--.

COLUMN 26

Line 31, "colour" should read --color--.

COLUMN 27

Line 65, "Crystallation" should read --Crystallization--.

UNITED STATES PATENT AND TRADEMARK OFFICE
CERTIFICATE OF CORRECTION

PATENT NO. : 5,006,570

DATED : April 9, 1991

INVENTOR(S) : JACQUELINE FRANCESCHINI, ET AL.

It is certified that error appears in the above-identified patent and that said Letters Patent is hereby corrected as shown below:

COLUMN 28

Line 23, "yield=74%." should read --yield=74%).--.

COLUMN 29

Line 66, "ph" should read --pH--.

COLUMN 31

Line 31, "behavioural" should read --behavioral--.

COLUMN 32

Line 11, "subcutaneouslyy" should read --subcutaneously--.

COLUMN 33

Line 47, "magnesium," should read --magnesium--.

COLUMN 34

Line 64, "cyclohexanylmethyl;" should read --cyclohexenylmethyl;--.

COLUMN 35

Line 1, "cyclohexyl-" should read --cyclohexenyl- --.

UNITED STATES PATENT AND TRADEMARK OFFICE
CERTIFICATE OF CORRECTION

PATENT NO. : 5,006,570

DATED : April 9, 1991

INVENTOR(S) : JACQUELINE FRANCESCHINI, ET AL.

It is certified that error appears in the above-identified patent and that said Letters Patent is hereby corrected as shown below:

COLUMN 36

Line 14, "claims 1," should read --claims 1 to 11,--.
Line 15, "2, 4, and 5-11" should be deleted.

Signed and Sealed this

Twenty-seventh Day of October, 1992

Attest:

DOUGLAS B. COMER

Attesting Officer     Acting Commissioner of Patents and Trademarks